(12) United States Patent
Sjoblom-Hallen et al.

(10) Patent No.: US 9,062,102 B2
(45) Date of Patent: Jun. 23, 2015

(54) ANTI OLIGOMER ANTIBODIES AND USES THEREOF

(75) Inventors: Anna Sjoblom-Hallen, Gothenburg (SE); Anders Sandberg, Gothenburg (SE)

(73) Assignee: ALZINOVA AG, Gothenburg (SE)

( * ) Notice: Subject to any disclaimer, the term of this patent is extended or adjusted under 35 U.S.C. 154(b) by 145 days.

(21) Appl. No.: 14/003,028

(22) PCT Filed: Mar. 7, 2012

(86) PCT No.: PCT/EP2012/053899
§ 371 (c)(1),
(2), (4) Date: Sep. 4, 2013

(87) PCT Pub. No.: WO2012/120035
PCT Pub. Date: Sep. 13, 2012

(65) Prior Publication Data
US 2013/0344089 A1    Dec. 26, 2013

Related U.S. Application Data

(60) Provisional application No. 61/450,235, filed on Mar. 8, 2011.

(30) Foreign Application Priority Data

Mar. 8, 2011 (EP) .................................... 11157301

(51) Int. Cl.
*C07K 16/18* (2006.01)
(52) U.S. Cl.
CPC ..................................... *C07K 16/18* (2013.01)
(58) Field of Classification Search
None
See application file for complete search history.

(56) References Cited

U.S. PATENT DOCUMENTS

| | | | |
|---|---|---|---|
| 2007/0218499 | A1 | 9/2007 | Lambert et al. |
| 2007/0258009 | A1 | 11/2007 | Kanda et al. |
| 2008/0065199 | A1 | 3/2008 | Lippoth et al. |
| 2009/0035307 | A1 | 2/2009 | Barghorn et al. |
| 2010/0150906 | A1 | 6/2010 | Pfeifer et al. |
| 2010/0209417 | A1 | 8/2010 | Lee et al. |
| 2011/0064741 | A1 | 3/2011 | Haerd |
| 2011/0212109 | A1 | 9/2011 | Barghorn et al. |

FOREIGN PATENT DOCUMENTS

| | | |
|---|---|---|
| WO | 2005/010049 A2 | 2/2005 |
| WO | 2008/067464 A2 | 6/2008 |
| WO | 2009/128772 A1 | 10/2009 |

OTHER PUBLICATIONS

Hillen Heinz, et. al., "Generation and Therapeutic Efficacy of Highly Oligomer-Specific beta-Amyloid Antibodies," Journal of Neuroscience, vol. 30, No. 31, Aug. 2010, pp. 10369-10379.
Brown McKay, et. al., "Tolerance to single but not multiple amino acid replacements in antibody V-H CDR2: A means of minimizing B cell wastage from somatic hypermutation?", Journal of Immunology, vo. 156, No. 9, Jan. 1, 1996, pp. 3285-3291.
Hardy, J., et. al, Trends Pharcol. Scie, 12(10), pp. 383-388 (1991).
Grandy, S., J. Clin. Invest. 115, pp. 1121-1129 (2005).
Jack, C.R., et. al., Lancet Neurol., 9, pp. 119-128 (2010).
Walsh, D.M., et. al., J. Neurochem., 101, pp. 1172-1184 (2007).
Sandberg, A., et. al., Proc. Natl. Acad. Sci. USA, 107, pp. 15595-15600 (2010).
Yoshiike, Y., et. al., PLoS ONE 3, e3235, (2008).
Kayed, R., et. al., Science 300, pp. 486-489, (2003).
Ogogozo, J-M., et. al., Neurology, 61, pp. 46-54 (2003).
Holmes, C. et al. (2008) Lancet 372:216-223.
Salloway, S. et al. (2009) Neurology 73:2061-2070.
Rinne, J.O., et al. (2010) Lancet Neurol. 9:363-372.
Siemers, ER. et al. (2010) Clin. Neuropharmacol. 33:67-73.
Abramov, E. et al. (2009) Nature Neurosci. 12:1567-1576.
Soscia, S.J. et al. (2010) PloS ONE 5(3):e9505.
The Human Protein Atlas at www.proteinatlas.org.
Uhlén M. et al. (2005) Mol. Cell. Proteomics 4:1920-1932.
Lindhagen-Persson, M. et al. (2010) PLoS ONE 5:e13928.
Kabat, E.A. et al. (1991) Sequences of Proteins of Immunological Interest, 5th Ed., National Insititutes of Health, Bethesda, MD, USA.
Chothia, C., and Lesk A. M. (1987) J. Mol. Biol. 196:901.
Chothia, C. et al. (1989) Nature 342:877.
Martin, A. C. et al. (1989) Proc. Natl. Acad. Sci. USA 86:9268.
http://www.bioinf-org.uk/abs.
Goldsbury, C. et al. (2005) J. Mol. Biol. 352:282-298.
Fernàndez-Tornero, C. et al. (2001) Nature Struct. Biol. 8:1020-1024.
Hermoso, J.A. et al. (2003) Structure 11:1239-1249.
Enya, M. et al. (1999) Am. J. Pathol. 154:271-279.
Shankar, G.M., et al. (2008) Nat. Med. 14:837-842.
O'Nuallain, B. et al. (2010) J. Neurosci. 30:14411-14419.
Severs, J.C. and Froland, W.A. (2008) J. Pharm. Sci. 97:1246-1256.
Tabner, B.J. et al. (2005) J. Biol. Chem. 280:35789-35792.
Doumaux Jr., A.R. et al. (1969) J. Am. Chem. Soc. 91:3992-3993.
Shapira, R. et al. (1988) J. Neurochem. 50:69-74.
Geiger, T. and Clarke, S. (1987) J. Biol. Chem. 262:785-794.
Harlow, E., and Lane, D., ed. Antibodies: A Laboratory Manual, Cold Spring Harbor, NY, (1998), p. 211-213.
Davidson, R.L., and Gerald, P.S. (1977) Methods Cell Biol. 15:325-338.
Ey, P.L., et al. (1978) Immunochem. 15:429-436.
Fezoui, Y. et al. (2000) Amyloid 7:166-178.
Stine, W.B. et al. (2003) J. Biol. Chem. 278:11612-11622.
Nilsberth, C. et al. (2001) Nat. Neurosci. 4:887-893.
Fukumoto, H., et al. (2010) FASEB J. 24:2716-2726.
International Search Report issued Apr. 23, 2012 in PCT/EP2012/053899.

*Primary Examiner* — Gregory S Emch
(74) *Attorney, Agent, or Firm* — Jeffrey S. Melcher; Manelli Selter PLLC

(57) ABSTRACT

The present invention relates to antibodies and antibody fragments specific for the toxic prefibrillar aggregates of amyloid-beta peptides, and uses thereof, for example in the diagnosis and treatment of amyloid diseases such as Alzheimer's disease and related disorders. The invention further provides methods for the identification of compounds potentially useful for the treatment of an amyloid disease, such as Alzheimer's disease.

9 Claims, 24 Drawing Sheets

ANTI OLIGOMER ANTIBODIES AND USES THEREOF

FIELD OF THE INVENTION

The present invention relates to antibodies specific for the toxic prefibrillar aggregates of amyloid-beta peptides, and uses thereof, for example in the diagnosis and treatment of amyloid diseases such as Alzheimer's disease and related disorders.

BACKGROUND OF THE INVENTION

Alzheimer's disease (AD) is a progressive neurological disorder characterized by the loss of synaptic function eventually leading to neuronal death. One of the main histopathological features in AD is the extracellular deposition of insoluble amyloid aggregates of the amyloid-β (Aβ) peptide in neuritic plaques, but it is still unclear exactly how these deposits relate to the etiology of AD. The Aβ peptide is generally 39-43 amino acids long, usually 40 or 42, and is continuously generated throughout most of the body as the transmembrane amyloid-β (A4) precursor protein (APP) is proteolytically processed during normal cell functioning. The "amyloid cascade hypothesis" states that the imbalance in the production of the Aβ protein and its clearance from the brain is the initiating event, subsequently leading to neurodegeneration and dementia (Hardy, J. and Allsop, D. (1991) *Trends Pharmacol. Sci.* 12(10):383-388). There is indeed ample evidence that an increased Aβ burden brought about by genetic mutations dramatically increases the risk of developing AD (Gandy, S. (2005) *J. Clin. Invest.* 115:1121-1129). Although less than 3% of all AD cases carry such pathogenic mutations, it is very likely that the progressively increasing burden of Aβ is also the causative and toxic agent in the sporadic form (97% of all AD cases). Available diagnostic data also support that the initiating event in AD is Aβ deposition in the brain, which is detectable as a decrease in $A\beta_{42}$ cerebral spinal fluid (CSF) levels (Jack, C. R. Jr. et al. (2010) *Lancet Neurol.* 9:119-128). This occurs well before the onset of symptoms, and pathology generally follows later. The increase in CSF "tau" (τ), on the other hand, is an indication of neurodegeneration—i.e. that nerve cells have already died, thus releasing the intracellular and hyperphosphorylated protein τ into the extracellular space. These elevated τ levels are only observed well after the onset of clinical symptoms. It thus follows that τ pathology probably succeeds Aβ pathology, and is most likely caused by it.

Although the Aβ peptide has been identified as the main culprit in AD, the mechanistic aspects of Aβ pathology remain elusive as Aβ has a high tendency to homo-oligomerize and is, in consequence, in a continuous equilibrium with higher-order aggregates. The result is a heterogeneous mix of monomeric, prefibrillar (both unstructured and with β-structure) and fibrillar oligomers of various sizes that continuously and irreversibly forms the insoluble fibrillar end state found in the plaques in AD patients' brains (a simplified aggregation scheme is depicted in FIG. 1). Recent data demonstrates that the oligomers of Aβ are particularly neurotoxic when compared to monomeric and fibrillar forms of the peptide and, therefore, that these oligomers are attractive therapeutic targets (Walsh, D. M. and Selkoe, D. J. (2007) *J. Neurochem.* 101:1172-84). The term "oligomer" is generally used to denote a molecule consisting of a plurality of monomers, and the term is herein reserved only for soluble species in order to distinguish them from the insoluble fibrils which are more polymeric than oligomeric. Herein, the terms "oligomer" and "soluble aggregate" are used interchangeably.

The oligomers formed by Aβ peptides during aggregation appear to be mainly of four types: (i) unstructured prefibrillar (of low-molecular weight, possibly micellar), (ii) prefibrillar with β-structure, (iii) prefibrillar of the "A11 positive" (A11+) type (of high-molecular weight, also containing β-structure), and (iv) fibrillar. These are schematically depicted in FIG. 1. Data on oligomers formed by the stabilized $A\beta_{42}$-A21C/A30C mutant ($A\beta_{42}$-CC), which renders the individual peptides incapable of adopting the fibrillar conformation, demonstrates that these prefibrillar oligomers with β-structure are 50 times more potent inducers of apoptosis than unstructured or fibrillar forms of the peptide (Sandberg, A. et al. (2010) *Proc. Natl. Acad. Sci. USA* 107:15595-15600). These oligomers are not of the A11+ type, and this result thus points to the prefibrillar oligomers with β-structure as the main mediators of Aβ toxicity. The A11+ aggregate has been suggested to be a special type of oligomer exposing a generic epitope found in several soluble aggregates of disease associated peptides and proteins (Kayed, R. et al. (2003) *Science* 300:486-489). The A11 epitope has also been found in native proteins as well, and it was thus suggested that it consists of exposed β-sheet edges (Yoshiike, Y. et al. (2008) *PLoS ONE* 3: e3235).

Although the exact etiological role of Aβ oligomers in AD is unknown, scientific evidence to date still points to the Aβ peptide as the most sensible target in AD therapy. However, many compounds and antibodies that have been effective against Aβ pathology in in vitro studies and in transgenic animal AD models have reached clinical trials, but none of them has proven effective in human Phase III trials. In consequence, current approved treatments for AD do not target Aβ specifically, but rather the underlying symptoms of the disease. These approved drugs are the acetylcholinesterase inhibitors and memantine (which is an N-methyl D-aspartate receptor antagonist).

Vaccination against the Aβ peptide was the first therapeutic strategy to exhibit efficacy in AD animal models. Naturally, clinical studies on AD patients ensued. But an early active vaccination trial on full-length partly aggregated $A\beta_{42}$, termed AN-1792, was halted after an increased incidence of aseptic meningoencephalitis in immunized patients (Orgogozo, J-M. et al. (2003) *Neurology* 61:46-54). This adverse inflammation response was thought to be triggered by Th1 T-cell epitopes in the C-terminal part of the peptide. Ongoing active vaccination trials (ACC001; and CAD106) have therefore focused on using Aβ N-terminal fragments only. Ongoing passive immunization trials using monoclonal antibodies that have reached Phase II or later (Bapineuzumab, Solanezumab, and PF4360365) are advantageous over active strategies in that specific epitopes can be targeted. However, both Bapineuzumab and Solanezumab also target all Aβ indiscriminately by binding to generic epitopes in the N-terminal part of the peptide. The rationale has instead been that passive immunization allows for an increased control of antibody titers and, perhaps more importantly, that any adverse effects are quickly reversed by simply discontinuing the administration of antibody. PF4360365 is unique in that it targets the C-terminal of $A\beta_{40}$ and not $A\beta_{42}$ at all.

One important outcome of these vaccination trials is that plaque removal alone cannot prevent disease progression. This has been demonstrated in both Bapineuzumab and the AN-1792 trials (Holmes, C. et al. (2008) *Lancet* 372:216-223; Salloway, S. et al. (2009) *Neurology* 73:2061-2070); Rinne, J. O., et al. (2010) *Lancet Neurol.* 9:363-372). Furthermore, neither Bapineuzumab nor Solanezumab treatment has thus far been able to improve cognition in treated AD patients (Salloway, S. et al. (2009) *Neurology* 73:2061-2070; Siemers, E R. et al. (2010) *Clin. Neuropharmacol.* 33:67-73). Indeed, the strategy to remove all forms of Aβ by targeting generic epitopes has thus far proven to be ineffective. Without wishing to be bound by any theory, the present inventors believe that this may be a reflection of (i) the increasing awareness that monomeric or fibrillar Aβ aggregates may not be the toxic agent in AD and, therefore, that (ii) huge titers are required to also target the much less prevalent toxic oligomeric structures. But simply increasing dosage of antibody to also target the oligomers may prove problematic, as large doses of Bapineuzumab was shown to increase the risk of vascogenic oedema (swelling of the brain related to changes in blood vessels) thus necessitating a reduction in dosage (Salloway, S. et al. (2009) *Neurology* 73:2061-2070). It was speculated that this swelling was caused by a disproportionate targeting of Aβ aggregates on blood vessels (a condition known as cerebral amyloid angiopathy).

In addition to these reservations, there is also some uncertainty relating to the potential side-effects of targeting all Aβ indiscriminately, as it has recently been shown that Aβ peptides may play a pivotal role in regulating presynaptic function (Abramov, E. et al. (2009) *Nature Neurosci.* 12:1567-1576) and/or that it may normally function in the innate immune system (Soscia, S. J. et al. (2010) *PloS ONE* 5(3): e9505). It is here also worth noting that the Aβ peptide is produced during normal cell metabolism throughout most of the body, and not only in neuronal cells although the expression levels appear to be somewhat higher in both neuronal and glandular cells (the Human Protein Atlas at www.proteinatlas.org; Uhlén M. et al. (2005) *Mol. Cell. Proteomics* 4:1920-1932).

Since oligomers were identified as the primary therapeutic target in AD, attempts have been made to isolate antibodies specific for oligomers but not fibrils or monomers. Several of these, most notably antibodies of the IgM type, appear to exhibit stronger binding to oligomers based on an avidity effect alone (Lindhagen-Persson, M. et al. (2010) *PLoS ONE* 5:e13928). It is possible that this avidity effect is the primary reason for the higher apparent affinity for oligomers exhibited by many of the antibodies proposed to be "conformation specific", even when these are of IgG type. Indeed, many of these antibodies also appear to bind fibrils, which is to be expected for such an effect. As an example: For the "conformation specific" antibody mAb158 one can still observe strong binding to fibrils (US 2009/0258009 A1). Other examples from prior art include antibodies 20C2 (US 2007/0218499 A1), hC2 (US 2010/0150906), 8F5hum8 (PCT/US 2008/065199), and NAB61 (US 2010/0209417 A1), which all exhibit high affinity for Aβ oligomers yet also display significant cross-reactivity with fibrils. Some of these "conformation specific" antibodies have now made it to human clinical trials. But it is at present still unclear if these antibodies exhibit a sufficiently high affinity for oligomers over monomers and/or fibrils in order for them not to be completely depleted by the preponderance of competing binding sites.

SUMMARY OF THE INVENTION

A strategy that circumvents the problems associated with the preponderance of competing antigens and the issue of also targeting functional Aβ focuses on developing therapeutics that specifically targets the toxic oligomers. In the case of antibody-based therapeutics, this requires antibodies with high specificity for a unique conformation found only in the prefibrillar oligomers with β-structure. Considering that the dominating form of Aβ in the blood is in the monomeric unstructured conformation, and in the brain presumably also in the fibrillar conformation, the ideal anti-oligomeric antibody would completely spare these non-toxic unstructured and fibrillar forms. A strong immune response specific for the prefibrillar oligomers with β-structure is required for the development of such oligomer-specific monoclonal antibodies, and this in turn requires stable and homogeneous antigen preparations. Such stable and homogeneous oligomers are also required for subsequent screening during antibody development. But, as discussed above, these oligomeric forms of Aβ are notoriously elusive because they are in a continuous equilibrium with higher-order oligomers and fibrils. The result is a heterogeneous mix of different forms of the peptide that continuously shifts towards the end state: the non-toxic insoluble fibrils. This poses a serious problem when oligomers are to be assayed specifically for identification of proteins and small-molecule binders/modifiers, and also if they are to be used to invoke an immune response against the toxic oligomeric forms.

If pure oligomers are desired, this problem of "metastability" must be overcome by stabilizing the oligomers, preferably covalently. The present inventors have identified the Aβ-CC peptides (described in WO 2009/128772, and in Sandberg, A. et al. (2010) *Proc. Natl. Acad. Sci. USA* 107: 15595-15600) as a possible solution to this problem. In Aβ-CC the conformational space available to the peptide is constrained, effectively inhibiting fibrillization. In consequence, $Aβ_{42}$-CC accumulates as toxic prefibrillar oligomers with β structure and $Aβ_{40}$-CC as low-molecular weight non-toxic oligomers and monomers which are largely unstructured.

The invention presented herein was developed by using $Aβ_{42}$-CC oligomers to invoke an immune response in mice, and this immune response was found to contain a strong oligomer specific component. This allowed for the selection of a monoclonal antibody that is highly specific for the toxic $Aβ_{42}$ oligomers with β-structure, herein termed mAb20. Such specificity for toxic aggregates makes this antibody superior to other non-specific vaccines as it spares both the functional (beneficial) non-aggregated Aβ peptides as well as fibrils, and allows for doses to be kept relatively low; both of which are also important factors in reducing the risk of vascogenic oedema in immunized patients.

Accordingly, the present invention provides binding proteins, such as antibodies, capable of binding to prefibrillar soluble aggregates of proteins or peptides, such as the Aβ peptide. Soluble aggregates of proteins are herein interchangeably also denoted oligomers. They consist of a plurality of self-assembled monomers, and appear to be generic toxins in higher organisms for reasons not clearly understood. For example, in Alzheimer's disease, oligomers of the Aβ peptide accumulate in the brain and causes neurodegeneration. These oligomers are therefore attractive therapeutic targets, but at the same time very difficult to isolate and study due to their inherent meta-stability.

The binding proteins provided according to the present invention are oligomer specific, and have been selected based on their selective binding to oligomeric forms of the $Aβ_{42}$-CC peptide. The present invention provides binding proteins and methods of producing and using these proteins or portions thereof.

One aspect of this invention provides binding proteins comprising a binding region capable of binding to $Aβ_{42}$ prefibrillar oligomers with β-structure. In one embodiment, this binding region comprises at least one amino acid sequence selected from the group consisting of:

GFSLSTFGSGVS  SEQ ID NO: 1

HIYWDDDKH  SEQ ID NO: 2

RESHYYGSGYYFDY  SEQ ID NO: 3

RASSSVSYMH  SEQ ID NO: 4

ATSNLAS  SEQ ID NO: 5

QQWRSDPLT,  SEQ ID NO: 6 and
an amino acid sequence having at least 80%, preferably 85%, more preferably 90%, or most preferably 95% sequence identity to SEQ ID NO:1, SEQ ID NO:2, SEQ ID NO:3, SEQ ID NO:4, SEQ ID NO:5 or SEQ ID NO:6.

SEQ ID NO:1 is the complementarity-determining region 1 (CDR1) of the variable heavy (VH) domain of the antibody mAb20; SEQ ID NO:2 is the CDR2 of the VH domain of mAb20, SEQ ID NO:3 is the CDR3 of the VH domain of mAb20. Similarly, SEQ ID NO:4 is the CDR1 of the variable light (VL$_\kappa$) domain of the antibody mAb20; SEQ ID NO:5 is the CDR2 of the variable light (VL$_\kappa$) domain of the antibody mAb20; SEQ ID NO:6 is the CDR3 of the variable light (VL$_\kappa$) domain of the antibody mAb20.

In one embodiment of the invention, the binding region of the binding protein comprises;
i) the amino acid sequences SEQ ID NO:1, or an amino acid sequence having at least 80%, preferably 85%, more preferably 90%, or most preferably 95% sequence identity to SEQ ID NO:1,
ii) the amino acid sequence SEQ ID NO:2, or an amino acid sequence having at least 80%, preferably 85%, more preferably 90%, or most preferably 95% sequence identity to SEQ ID NO:2, and
iii) the amino acid sequence SEQ ID NO:3, or an amino acid sequence having at least 80%, preferably 85%, more preferably 90%, or most preferably 95% sequence identity to SEQ ID NO:3.

In another embodiment of the invention, the binding region of the binding protein comprises;
i) the amino acid sequences SEQ ID NO:4, or an amino acid sequence having at least 80%, preferably 85%, more preferably 90%, or most preferably 95% sequence identity to SEQ ID NO:4,
ii) the amino acid sequence SEQ ID NO:5, or an amino acid sequence having at least 80%, preferably 85%, more preferably 90%, or most preferably 95% sequence identity to SEQ ID NO:5, and
iii) the amino acid sequence SEQ ID NO:6, or an amino acid sequence having at least 80%, preferably 85%, more preferably 90%, or most preferably 95% sequence identity to SEQ ID NO:6.

In yet another preferred embodiment of the invention, the binding region of the binding protein comprises;
i) the amino acid sequences SEQ ID NO:1, or an amino acid sequence having at least 80%, preferably 85%, more preferably 90%, or most preferably 95% sequence identity to SEQ ID NO:1
ii) the amino acid sequence SEQ ID NO:2, or an amino acid sequence having at least 80%, preferably 85%, more preferably 90%, or most preferably 95% sequence identity to SEQ ID NO:2,
iii) the amino acid sequence SEQ ID NO:3, or an amino acid sequence having at least 80%, preferably 85%, more preferably 90%, or most preferably 95% sequence identity to SEQ ID NO:3
iv) the amino acid sequences SEQ ID NO:4, or an amino acid sequence having at least 80%, preferably 85%, more preferably 90%, or most preferably 95% sequence identity to SEQ ID NO:4,
v) the amino acid sequence SEQ ID NO:5, or an amino acid sequence having at least 80%, preferably 85%, more preferably 90%, or most preferably 95% sequence identity to SEQ ID NO:5, and
vi) the amino acid sequence SEQ ID NO:6, or an amino acid sequence having at least 80%, preferably 85%, more preferably 90%, or most preferably 95% sequence identity to SEQ ID NO:6.

Preferably the binding region of the binding protein comprises the CDR1, the CDR2, and the CDR3 of the variable heavy (VH) domain of the antibody mAb20, i.e. the binding region of the binding protein comprises the amino acid sequences SEQ NO:1, SEQ ID NO: 2, and SEQ ID NO:3.

Preferably the binding region of the binding protein comprises the CDR1, the CDR2, and the CDR3 of the variable light (VL) domain of the antibody mAb20, i.e. the binding region of the binding protein comprises the amino acid sequences SEQ NO:4, SEQ ID NO: 5, and SEQ ID NO:6.

More preferably the binding region of the binding protein comprises the CDR1, the CDR2, and the CDR3 of the variable heavy (VH) domain, and the CDR1, the CDR2, and the CDR3 of the variable light (VL) domain of the antibody mAb20, i.e. the binding region of the binding protein comprises the amino acid sequences SEQ NO:1, SEQ ID NO: 2, SEQ ID NO:3, SEQ NO:4, SEQ ID NO: 5, and SEQ ID NO:6.

The binding proteins according to the present invention can be selected from antibodies, antibody fragments, and non-antibody binding proteins.

Preferably the binding protein is an antibody or antibody fragment that comprises a variable heavy (VH) domain having the amino acid SEQ ID NO:1 as CDR1, the amino acid SEQ ID NO:2 as CDR2, and the amino acid sequence SEQ ID NO:3 as CDR3.

Preferably the binding protein is an antibody or antibody fragment that comprises a variable light (VL) domain having the amino acid SEQ ID NO:4 as CDR1, the amino acid SEQ ID NO:5 as CDR2, and the amino acid sequence SEQ ID NO:6 as CDR3.

More preferably the binding protein is an antibody or antibody fragment that comprises a variable heavy (VH) domain having the amino acid SEQ ID NO:1 as CDR1, the amino acid SEQ ID NO:2 as CDR2, and the amino acid sequence SEQ ID NO: 3 as CDR3, and variable light (VL) domain having the amino acid SEQ ID NO:4 as CDR1, the amino acid SEQ ID NO:5 as CDR2, and the amino acid sequence SEQ ID NO:6 as CDR3.

In the antibody or antibody fragment according to the foregoing embodiments, it may be preferred that the VH domain, the VL domain, or preferably both of the VH and VL domains, comprise CDRs comprising an amino acid sequence having 100% sequence identity to the stated SEQ ID NO.

Alternatively, the VH domain, the VL domain, or both of the VH and VL domains, may comprise CDRs comprising an amino acid sequence having less than 100%, but at least 80%, 85%, 90%, 95%, sequence identity to the stated SEQ ID NO.

A CDR comprising an amino acid sequence having less than 100% but at least 80%, 85%, 90%, 95%, sequence identity to the stated SEQ ID NO may be a sequence possessing one or more sequence variations compared to the stated SEQ ID NO. Variations in sequence may be due to one or more amino acid additions, one or more amino acid deletions and/or one or more amino acid substitutions compared to the stated SEQ ID NO. Where there is more than one variation, then the variations may be in consecutive or non-consecutive positions.

Substitutions may be conservative or non-conservative substitutions. By "conservative substitutions" is intended combinations such as Gly, Ala; Val, Ile, Leu; Asp, Glu; Asn, Gln; Ser, Thr; Lys, Arg; and Phe, Tyr.

Sequence variations may, for example, be introduced in order to render the sequence of the antigen binding region(s) closer to germline sequences, to improve the stability of the antibody or antibody fragment comprising the variant antigen binding region(s), to reduce the immunogenicity of the antibody or antibody fragment comprising the variant antigen binding region(s), and/or to avoid or reduce properties that could be disadvantageous in the manufacturing process.

Such variants may be made using the methods of protein engineering and site-directed mutagenesis or alternative methods that are well known in the art.

Where the VH domain, the VL domain, or both of the VH and VL domains, of the antibody or antibody fragment of the present invention comprise(s) a CDR having an amino acid sequence having less than 100%, but at least 80%, 85%, 90%, 95%, sequence identity to the stated SEQ ID NO, then in one embodiment the ability of the antibody or antibody fragment to bind to Aβ42 prefibrillar oligomers with β-structure may, for example, be substantially equivalent to, that is, at least 80%, 85%, 90% or 95%, of the ability of a corresponding 'parent' antibody or antibody fragment, wherein the CDRs of VH domain and the VL domain of the corresponding 'parent' antibody or antibody fragment each comprise an amino acid sequence having 100% sequence identity to the stated SEQ ID NO.

In this regard, the ability of an antibody or antibody fragment to bind to Aβ42 prefibrillar oligomers with β-structure may be determined by any suitable method, such as by Surface Plasmon Resonance (SPR) analysis, to measure the binding of the antibody or antibody fragment to Aβ42 prefibrillar oligomers with β-structure immobilized to a solid surface such as the Biacore SPR biosensor.

Accordingly, one aspect of this invention provides an antibody or antibody fragment capable of binding to Aβ42 prefibrillar oligomers with β-structure, wherein the antibody or antibody fragment comprises a variable heavy (VH) domain and/or a variable light (VL) domain, and where
  a) the variable heavy (VH) domain comprises an amino acid sequence that includes one, two or three complementary determining regions (CDRs) selected from the group consisting of:
    a CDR1 comprising an amino acid sequence having at least 80%, 85%, 90%, 95% or 100% sequence identity to SEQ ID NO:1,
    a CDR2 comprising an amino acid sequence having at least 80%, 85%, 90%, 95% or 100% sequence identity to SEQ ID NO:2, and
    a CDR3 comprising an amino acid sequence having at least 80%, 85%, 90%, 95% or 100% sequence identity to SEQ ID NO:3 as CDR3, and/or
  b) the variable light (VL) domain comprises an amino acid sequence that includes one, two or three complementary determining regions (CDRs) selected from the group consisting of:
    a CDR1 comprising an amino acid sequence having at least 80%, 85%, 90%, 95% or 100% sequence identity to SEQ ID NO:4,
    a CDR2 comprising an amino acid sequence having at least 80%, 85%, 90%, 95% or 100% sequence identity to SEQ ID NO:5, and
    a CDR3 comprising an amino acid sequence having at least 80%, 85%, 90%, 95% or 100% sequence identity to SEQ ID NO:6.

Preferably the antibody or antibody fragment comprises
  a) a variable heavy (VH) domain having an amino acid sequence having at least 80%, 85%, 90%, 95% or 100% sequence identity to SEQ ID NO:1 as CDR1, an amino acid sequence having at least 80%, 85%, 90%, 95% or 100% sequence identity to SEQ ID NO:2 as CDR2, and an amino acid sequence having at least 80%, 85%, 90%, 95% or 100% sequence identity to SEQ ID NO:3 as CDR3, and/or
  b) a variable light (VL) domain having an amino acid sequence having at least 80%, 85%, 90%, 95% or 100% sequence identity to SEQ ID NO:4 as CDR1, an amino acid sequence having at least 80%, 85%, 90%, 95% or 100% sequence identity to SEQ ID NO:5 as CDR2, and an amino acid sequence having at least 80%, 85%, 90%, 95% or 100% sequence identity to SEQ ID NO:6 as CDR3.

Even more preferably the binding protein is an antibody or antibody fragment that comprises a variable heavy (VH) domain having the amino acid sequence SEQ ID NO:8.

Even more preferably the binding protein is an antibody or antibody fragment that comprises a variable light (VL) domain having the amino acid sequence SEQ ID NO:10.

Most preferably the binding protein is an antibody or antibody fragment that comprises a variable heavy (VH) domain having the amino acid sequence SEQ ID NO:8, and a variable light (VL) domain having the amino acid sequence SEQ ID NO:10.

Preferably the binding protein is an antibody.

Preferably the antibody is a monoclonal antibody, such as the monoclonal antibody mAb20.

The antibody can be a humanized antibody or a chimeric antibody.

Preferably the antibody is an isolated antibody.

One or more of the CDRs described above can be grafted onto various protein scaffolds of immunoglobulins or other binding-proteins using standard protein engineering techniques. The end result is preserved antigen-binding activity in a new (surrogate) framework.

The scaffolds of immunoglobulins can be derived from IgA1, IgA2, IgD, IgE, IgG1, IgG2, IgG3, IgG4, IgM. The scaffolds can be derived from an immunoglobulin from any mammal, such as mice, rats, rabbits, goats, camels, llamas, primates. Preferably the immunoglobulin scaffold is derived from human immunoglobulins.

The scaffolds of non-antibody binding-proteins can be derived from several non-antibody binding-proteins, of which over 50 have been proposed (Skerra, A. (2007) *Curr. Opin. Biotechnol.* 18:295-304) including but not limited to: fibronectin type III, lipocalin, protein Z, thioredoxin A, ankyrin repeats, γ/β crystallin, tetranectins, PIN (protein inhibitors of neuronal NO synthase), and neocarcinostatin.

The antibody fragments according to the invention can be generated by standard molecular biology techniques or by cleavage of purified antibodies using enzymes (e.g. pepsin or papain) that generates these fragments. Such antibody fragments according to the invention are exemplified, but not limited to, single chain antibodies, Fv, scFv, Fab, F(ab')$_2$, Fab', Fd, dAb, CDR, or scFv-Fc fragments or nanobodies, and diabodies, or any fragment that may have been stabilized by e.g. PEGylation.

Another aspect of the present invention provides a pharmaceutical composition comprising a binding protein according to the invention and a pharmaceutically acceptable carrier or excipient.

Another aspect of the present invention provides a pharmaceutical composition comprising a binding protein according to the invention and a pharmaceutically acceptable carrier or excipient for use in the prevention, prophylaxis and/or treatment of an amyloid disease, preferably Alzheimer's disease.

Yet another aspect of the present invention provides use of a binding protein according to the invention in the manufacture of a pharmaceutical composition for the prevention, prophylaxis and/or treatment of an amyloid disease, preferably Alzheimer's disease.

Another aspect of the present invention provides a method for the prevention, prophylaxis and/or treatment of an amyloid disease, preferably Alzheimer's disease, comprising administering a pharmaceutical effective amount of a binding protein according to the invention to a subject in need of such treatment.

Yet another aspect of the present invention provides use of a binding protein according to the invention in the diagnosis of an amyloid disease, preferably Alzheimer's disease.

Yet another aspect of the present invention provides a method for the diagnosis of an amyloid disease, preferably Alzheimer's disease, comprising the use of a binding protein according to the invention. The method is preferably an immunological method. The method is preferably an in vitro method performed on a sample obtained from a subject. Preferable the subject is a human.

Yet another aspect of the present invention provides a method comprising the use of a binding protein according to the invention for use in screening assays aimed at identifying chemical substances, such as small-molecules, peptides and/or proteins, potentially useful in treatment of an amyloid disease, preferably Alzheimer's disease. In one such embodiment the present invention provides an assay, comprising the use of a binding protein according to the invention, for identifying chemical substances which affect the aggregation process of amyloidogenic peptides and proteins. Preferably, the amyloidogenic peptide is Aβ.

Said assay can comprise:
c) providing a test compound,
d) adding said test compound to a solution of amyloidogenic peptides or pre-formed toxic aggregates of the same peptide,
e) determining if the test compound affects the aggregation of said peptide, or if it affects the stability of pre-formed toxic aggregates of the peptide, by assaying for the existence of aggregates reactive against a binding protein according to the invention,
f) identifying said compound as potentially suitable for the treatment of a disease caused by or related to the formation of toxic aggregates of the peptide.

Yet another aspect of the present invention provides nucleic acid sequences encoding a binding protein according to the invention.

Yet another aspect of the present invention provides a vector comprising a nucleic acid sequence according to the invention.

Yet another aspect of the present invention provides a host cell comprising a vector according to the invention.

The host cell can be a prokaryotic cell, such as an Escherichia coli cell.

The host cell can be an eukaryotic cell, such as animal cell, a plant cell, and a fungal cell.

The animal cell can be a mammalian cell, an avian cell, and an insect cell.

The mammalian cell can be a CHO cell, and a COS cell.

The fungal cell can be a yeast cell, such as a *Saccharomyces cerevisiae* cell.

Yet another aspect of the present invention provides a method for producing a binding protein comprising an antigen-binding region capable of binding to $A\beta_{42}$ prefibrillar oligomers comprising culturing a host cell according to the invention.

Figure 2:
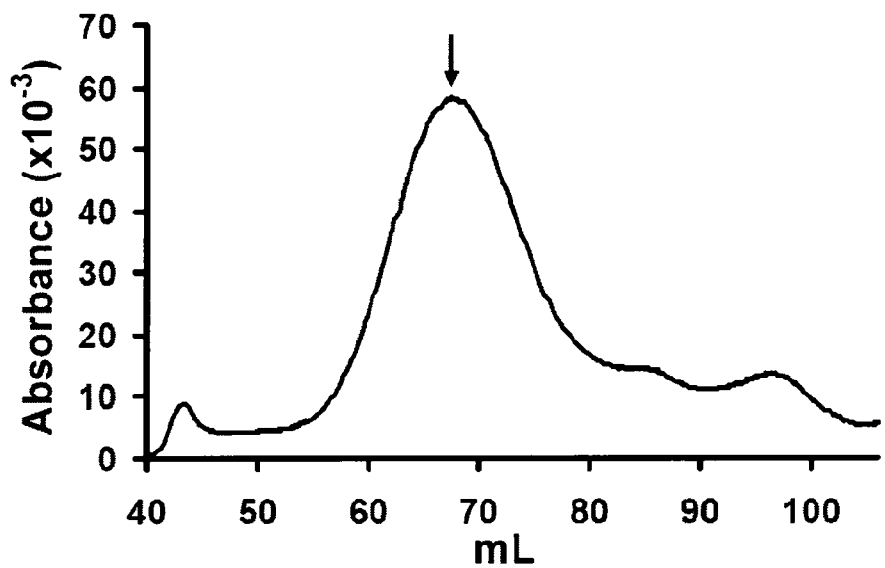
FIG. 2. Characteristics of the oligomers used in the present invention. (A) A typical size-exclusion chromatography profile obtained during preparation of $A\beta_{42}$-CC oligomers. This mutant elutes as approximately 100 kDa proteins (marked by an arrow), likely corresponding to dodecameric oligomers. (B) An absorbance spectrum collected on concentrated $A\beta_{42}$-CC oligomers lacks light-scattering artefacts in the far-UV region. (C) A transmission electron micrograph of concentrated $A\beta_{42}$-CC oligomers. These structures are similar to oligomers formed by $A\beta_{42}$ and $A\beta_{40}$ wild-type peptides, as well as those formed by E22G mutant derivatives (the Arctic mutation). (D) An aggregation assay of $A\beta_{42}$-CC oligomers with (+TCEP) and without (−TCEP) reductant. This assay monitors Thioflavin-T fluorescence. The oligomers are extremely stable, and only form Thioflavin-T positive fibrils in the presence of TCEP which breaks the stabilizing intramolecular disulfide bond. Baselines containing only TCEP and buffer coincide with the "−TCEP" sample in this figure.
Figure 2:
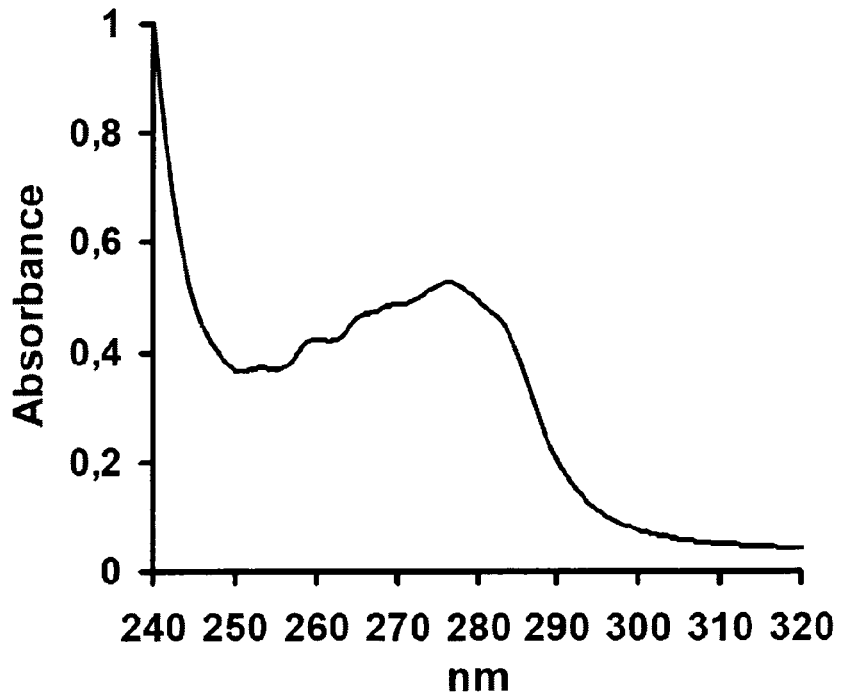
Figure 2:
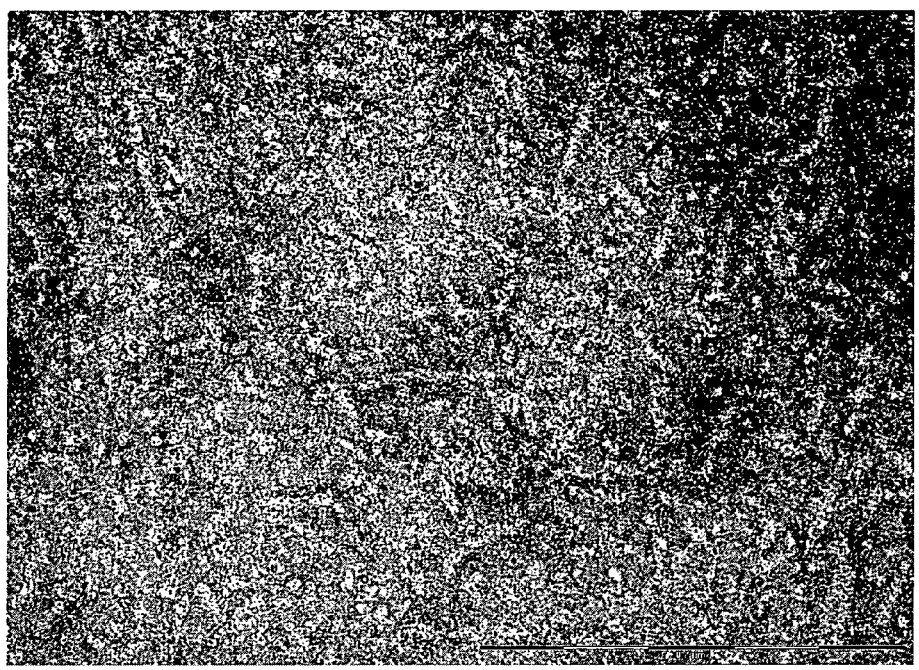
Figure 2:
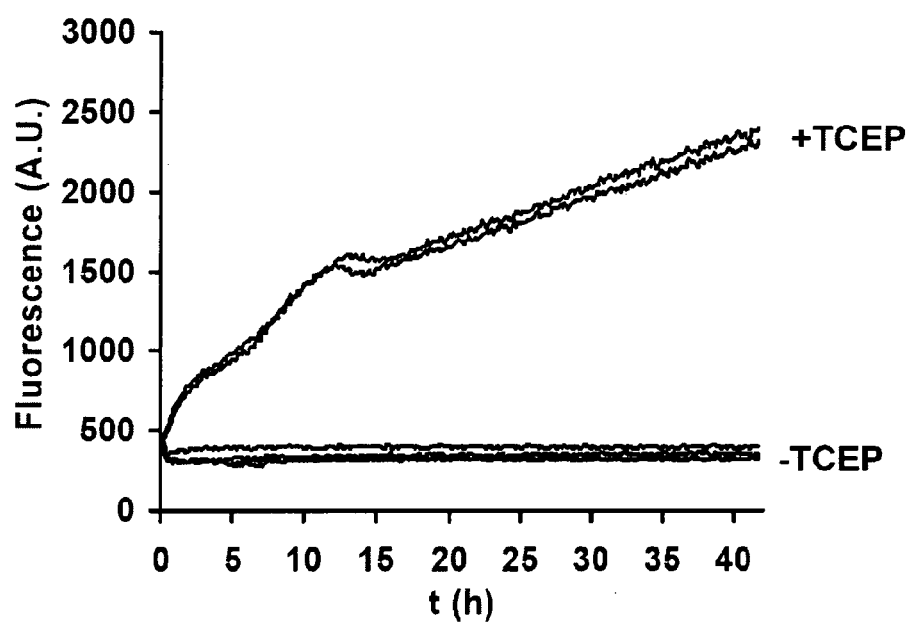
Figure 6:
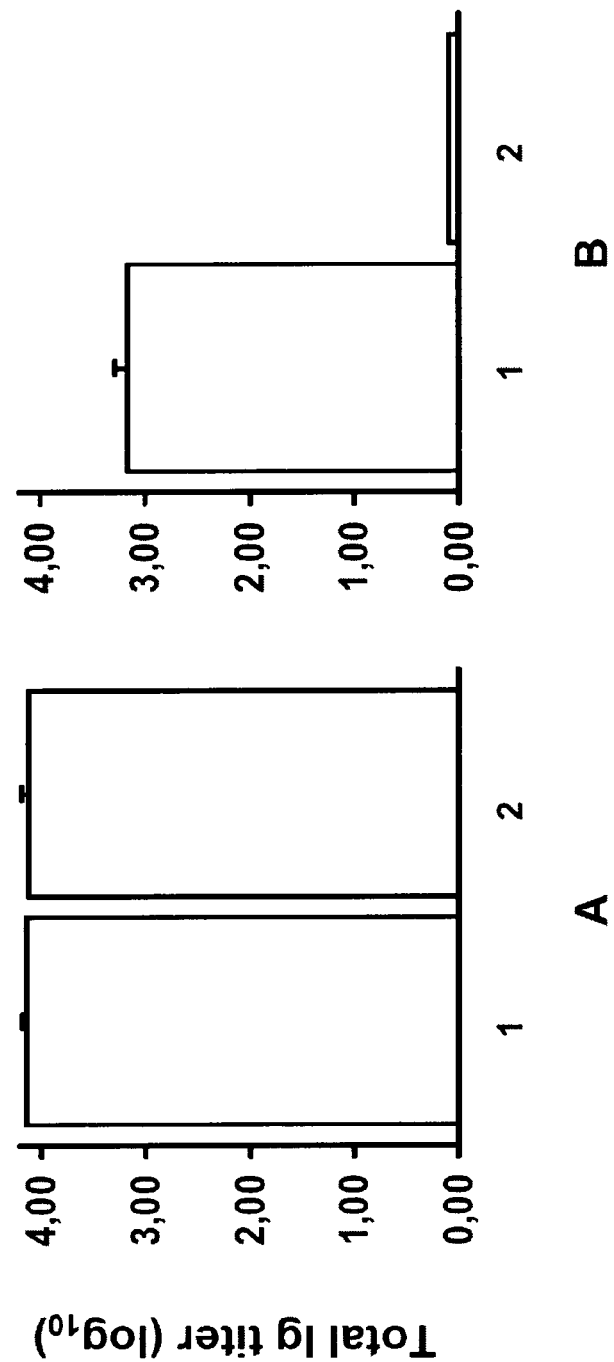

FIG. 6. Titers from a direct ELISA on polyclonal serum obtained by immunization using the oligomers presented in FIG. 2. Antigens coated were (1) Aβ$_{42}$-CC oligomers and (2) Aβ$_{42}$-CC monomers. In this experiment, serum was treated with a suspension of insoluble Aβ fibrils. Antibodies that bound to the fibrils were then removed by centrifugation. The supernatant of the fibril-treated serum in panel (B) was found to contain a strong oligomer-specific component when compared with untreated serum in panel (A). This method thus produces a type of oligomer-specific polyclonal serum.

Figure 7:
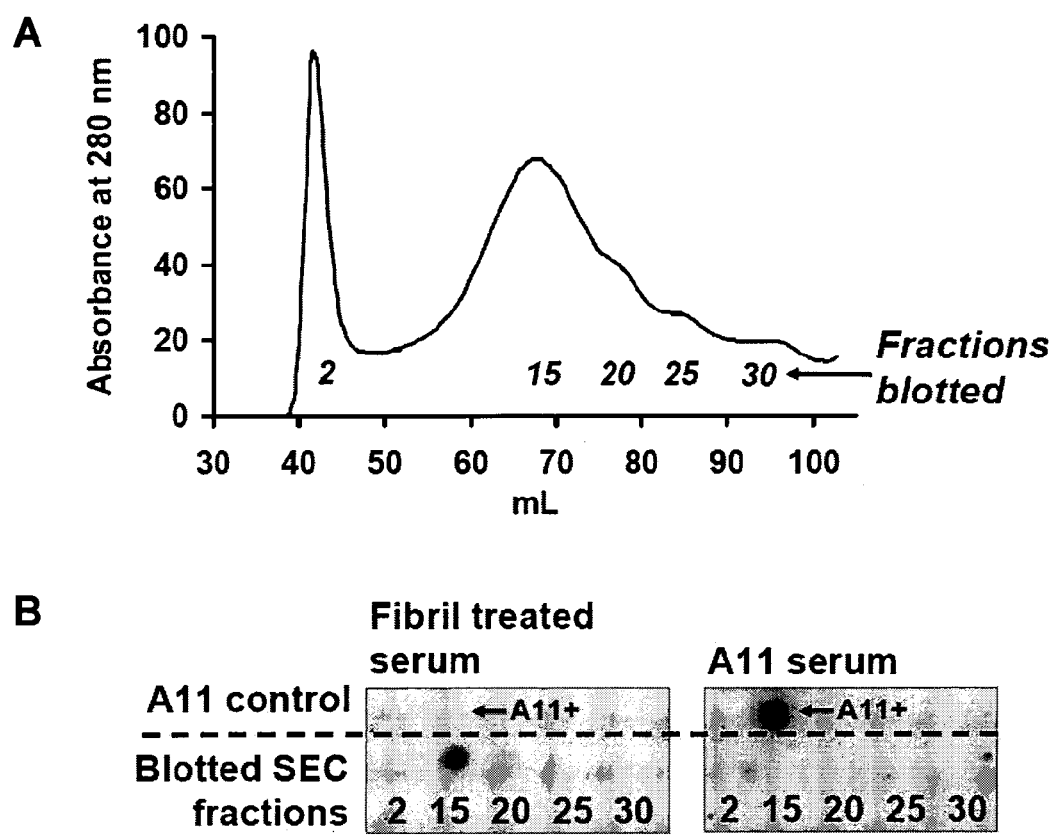

FIG. 7. An experiment that shows that the oligomer-specific component of fibril-treated serum (cf. FIG. 6) binds exclusively to prefibrillar Aβ$_{42}$ oligomers with β-structure. (A) SEC profile obtained during preparation of Aβ$_{42}$-CC oligomers. Fractions 2, 15, 20, 25, and 30 were dot blotted. (B) Dot blot of the fractions in A together with an A11 positive control. The left and right membranes were treated with fibril-treated serum and the A11 serum, respectively. The Aβ$_{42}$-CC oligomers are distinct from the A11 positive oligomers, and the oligomer-specific polyclonal serum only recognizes prefibrillar oligomers with β-structure.

Figure 8:
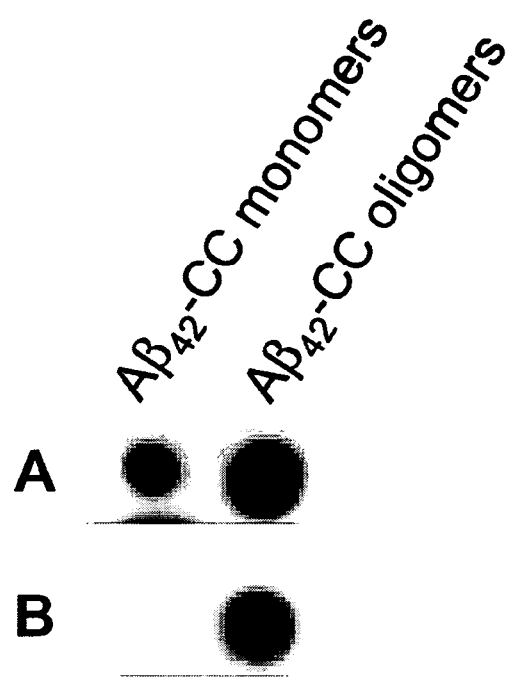

FIG. 8. A dot blot against equal amounts of Aβ$_{42}$-CC monomers (left sample) and Aβ$_{42}$-CC oligomers (right sample) of polyclonal serum obtained by immunization using Aβ$_{42}$-CC oligomers (membrane A) compared with a dotblot where the same polyclonal serum was pre-treated with Aβ$_{40}$-CC (membrane B). Clearly, adding excessive unstructured Aβ$_{40}$-CC has the same effect as pre-treating the serum with fibrils (cf. FIGS. 6 and 7).

Figure 9:
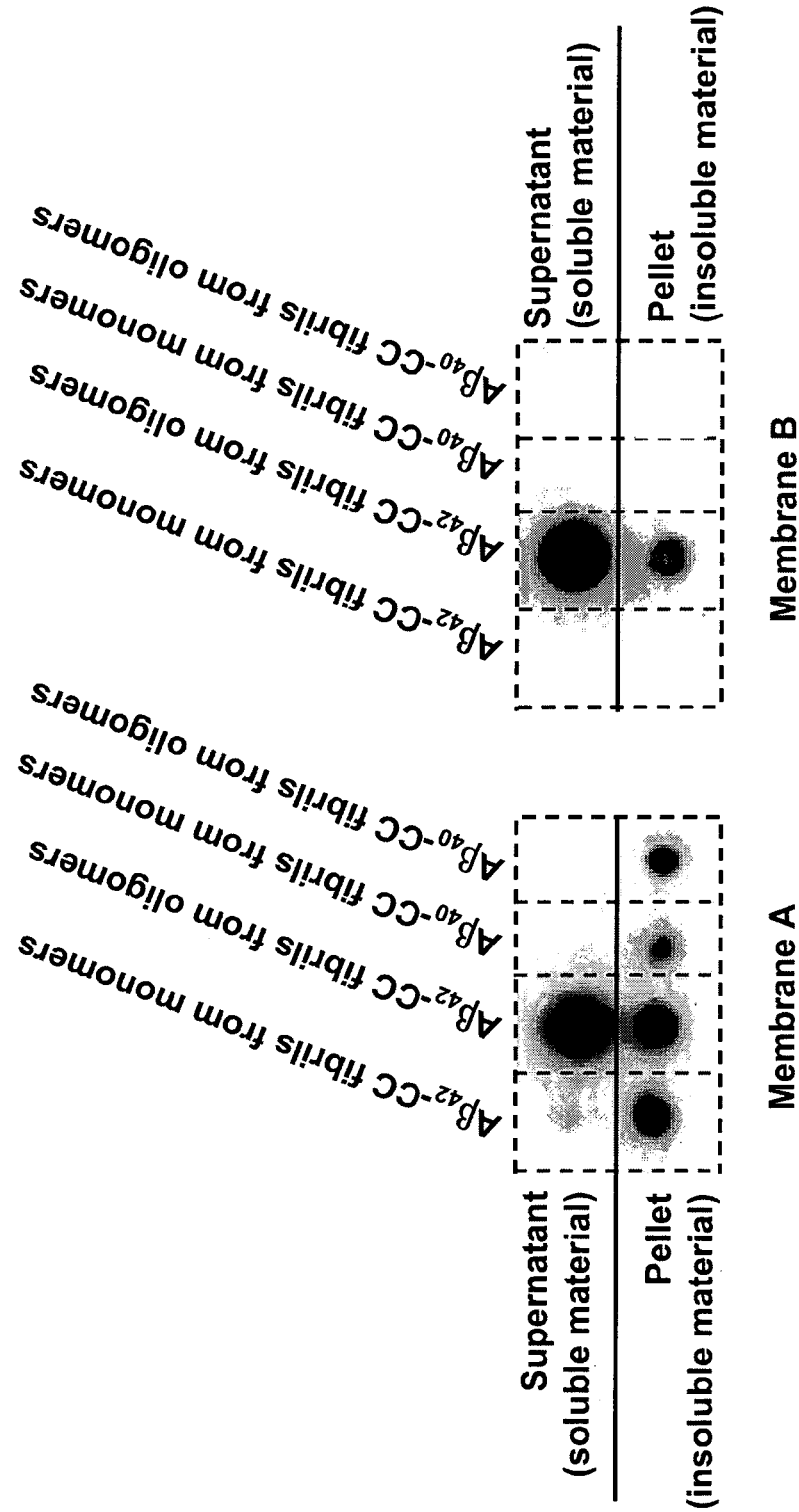

FIG. 9. Membrane (A) shows a dot blot against fibrillar (reduced) Aβ-CC of polyclonal serum obtained by immunization using Aβ$_{42}$-CC oligomers. Membrane (B) shows a dot blot of the same serum pre-treated with Aβ$_{40}$-CC. This dot blot shows that polyclonal serum does not recognize fibrils in the presence of unstructured Aβ$_{40}$-CC.

Figure 10:
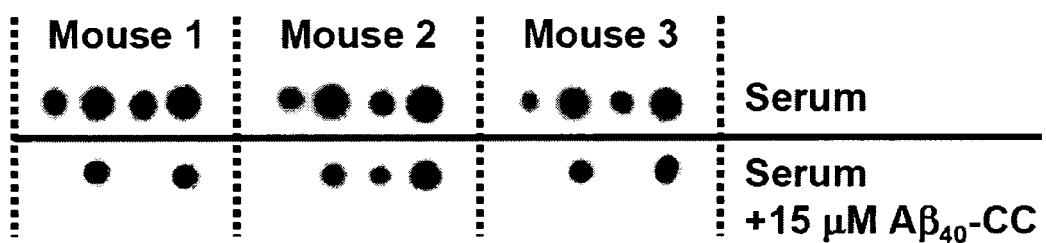

FIG. 10. Dot blots of polyclonal serum from three mice obtained by an immunization protocol using Freunds adjuvance and Aβ$_{42}$-CC oligomers. On each membrane, from left to right, were blotted equal amounts of: Aβ$_{40}$-CC monomers, Aβ$_{40}$-CC oligomers, Aβ$_{42}$-CC monomers, and Aβ$_{42}$-CC oligomers. The top membranes were treated with serum diluted 1:1000, and the bottom membranes were treated with serum similarly diluted and supplemented with 15 µM Aβ$_{40}$-CC monomers. The excessive presence of unstructured Aβ$_{40}$-CC reveals a strong oligomer-specific component, and two mice were therefore selected for monoclonal antibody development.

Figure 11:
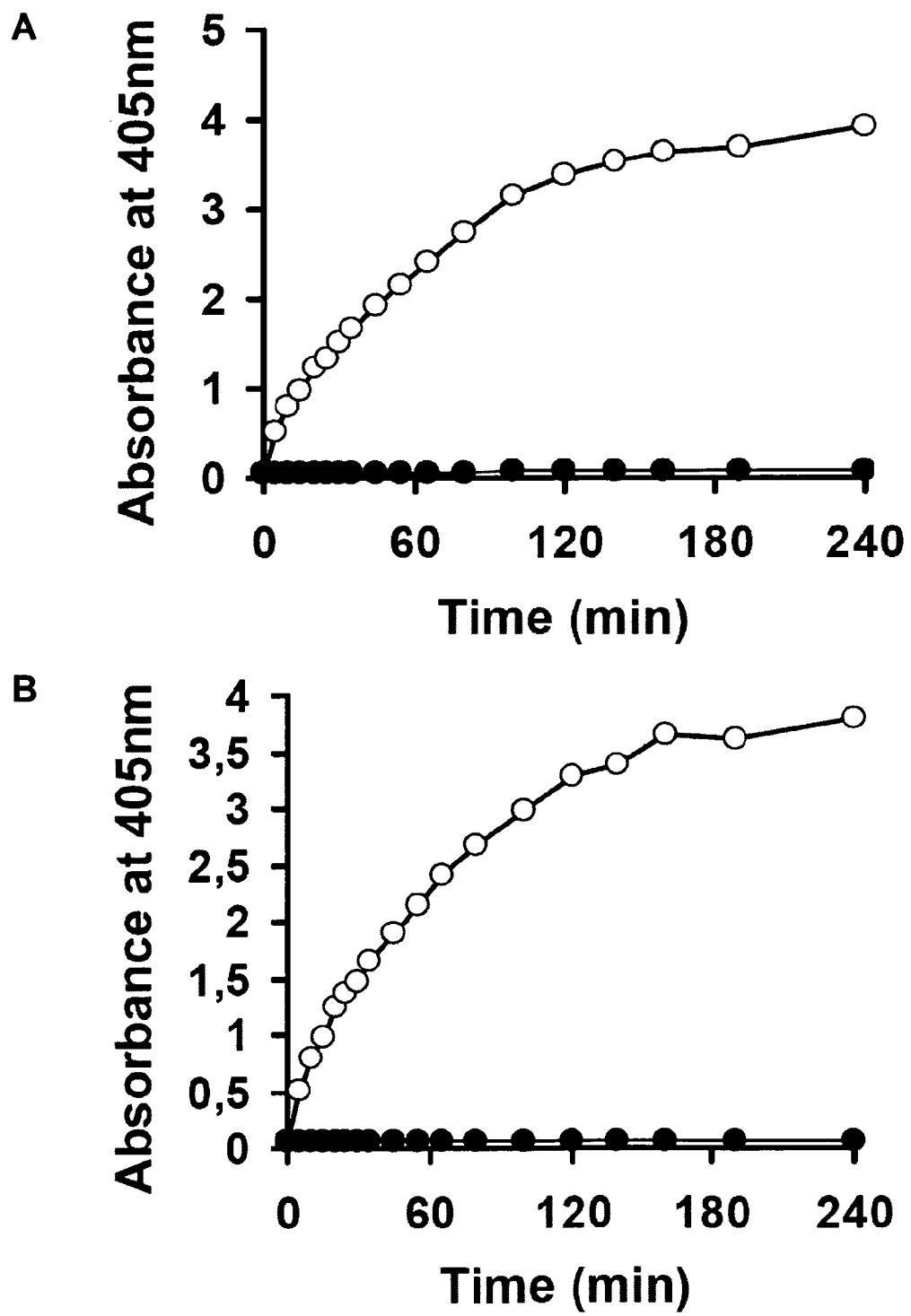
Figure 11:
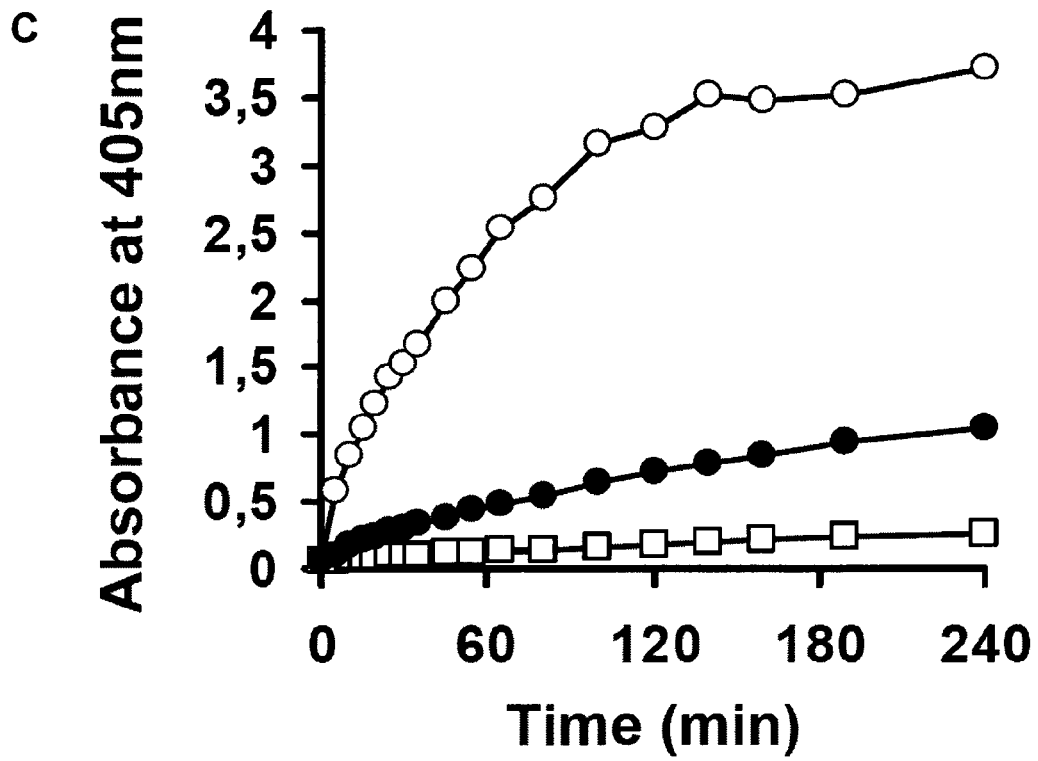
Figure 11:
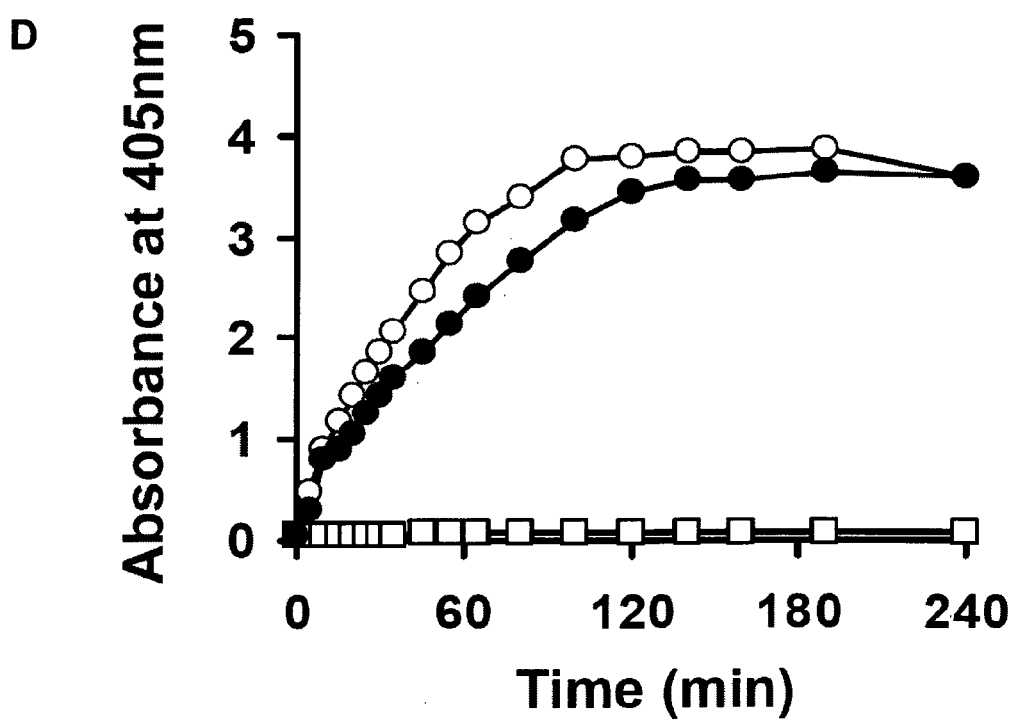

FIG. 11. A direct ELISA of serum from hybridoma 20 expressing the monoclonal antibody mAb20. A strong signal is only obtained against Aβ$_{42}$-CC oligomers. Antigens coated were (A) Aβ$_{40}$-CC monomers, (B) Aβ$_{40}$-CC oligomers, (C) Aβ$_{42}$-CC monomers, and (D) Aβ$_{42}$-CC oligomers. (-○-) The antibody 6E10; (-●-) mAb20, (-□-) baseline. The 6E10 antibody recognizes the unstructured N-terminal of nearly all forms of Aβ.

Figure 12:
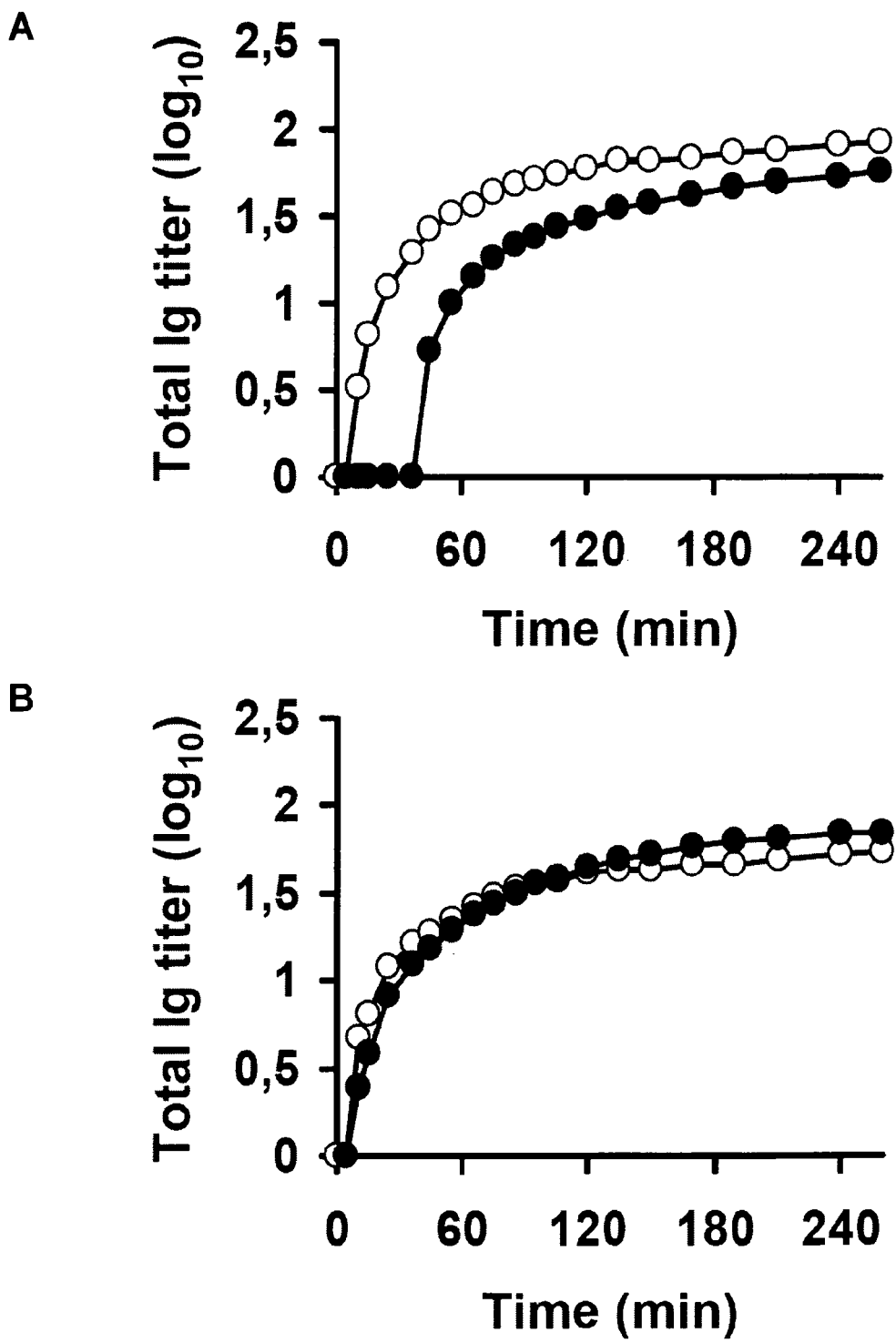

FIG. 12. Titers from the direct ELISA in FIG. 11 against Aβ$_{42}$-CC monomers (A) and oligomers (B). (-○-) The antibody 6E10; (-●-) mAb20.

Figure 13:
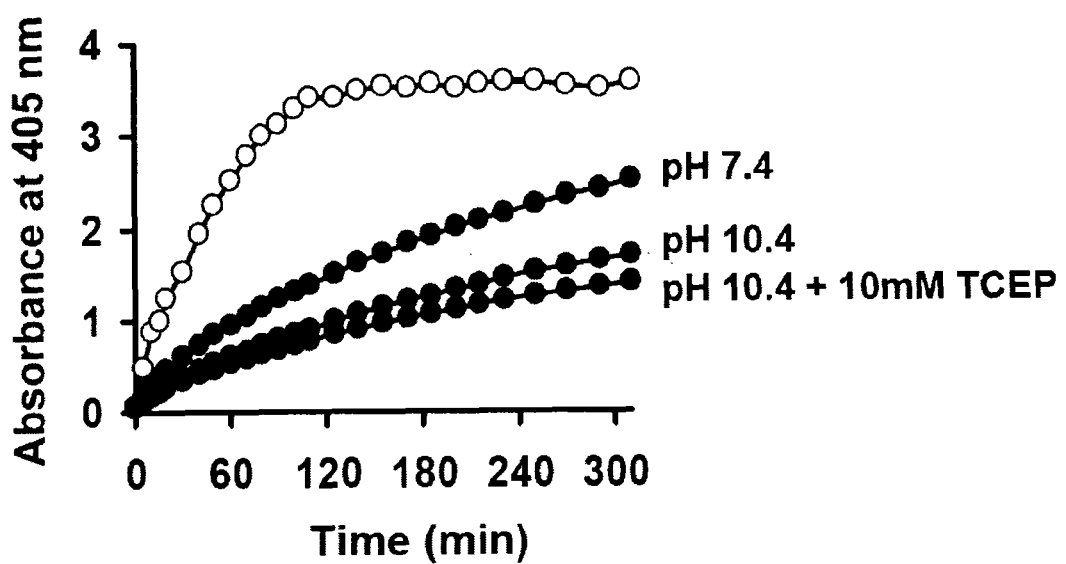

FIG. 13. A direct ELISA of serum from hybridoma 20 expressing the monoclonal antibody mAb20. Aβ$_{42}$-CC monomers were immobilized under different pH conditions, where a high pH helps to maintain Aβ in monomeric form. Aβ$_{42}$-CC monomers were also assayed in reduced form (+TCEP). (-○-) The antibody 6E10; (-●-) mAb20. The monoclonal antibody 6E10 was used as reference. The 6E10 antibody recognizes the unstructured N-terminal of nearly all forms of Aβ. A11 data proved similar for the 6E10 antibody (only one curve is shown).

Figure 14:
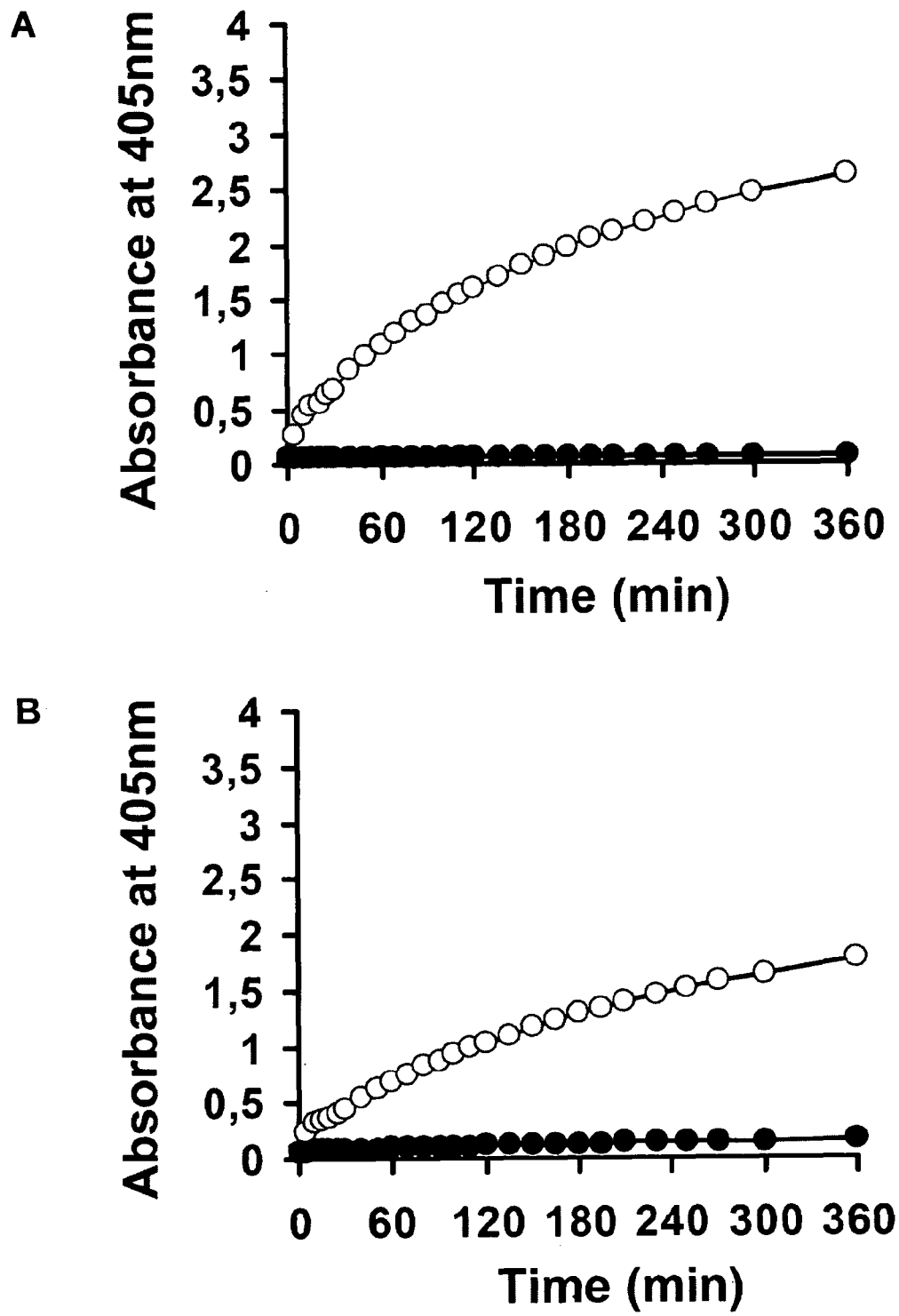

FIG. 14. A direct ELISA of serum from hybridoma 20 expressing the monoclonal antibody mAb20 against (A) Aβ$_{40}$-CC fibrils (reduced) and (B) Aβ$_{42}$-CC fibrils (reduced). (-○-) The antibody 6E10; (-●-) mAb20. Clearly, mAb20 does not recognize fibrils of either Aβ$_{40}$ or Aβ$_{42}$. The monoclonal antibody 6E10 was used as reference. The 6E10 antibody recognizes the unstructured N-terminal of nearly all forms of Aβ.

Figure 15:
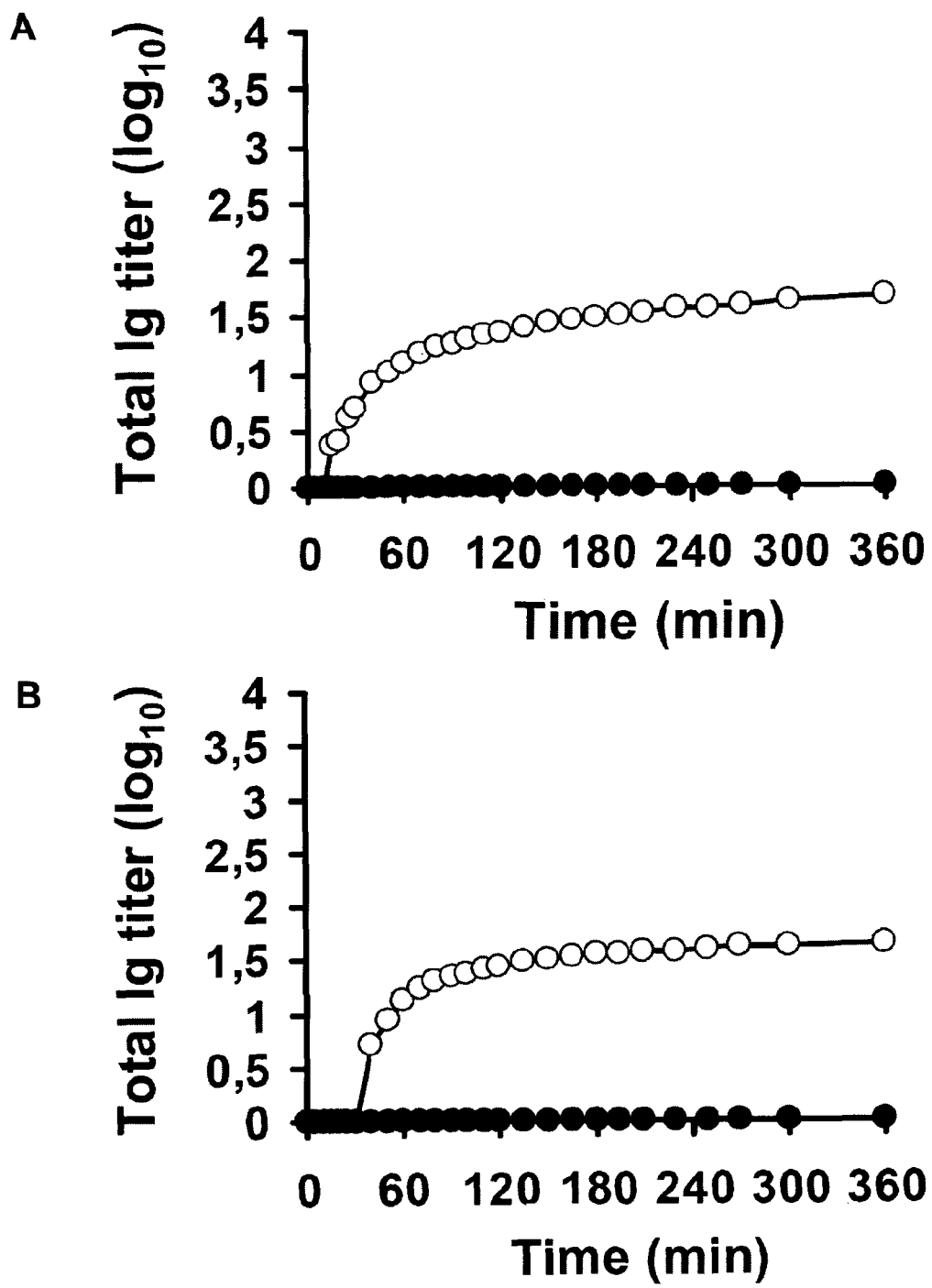

FIG. 15. Titers from the direct ELISA in FIG. 14 against (A) Aβ$_{42}$-CC monomers and (B) oligomers. (-○-) The antibody 6E10; (-●-) mAb20.

Figure 16:
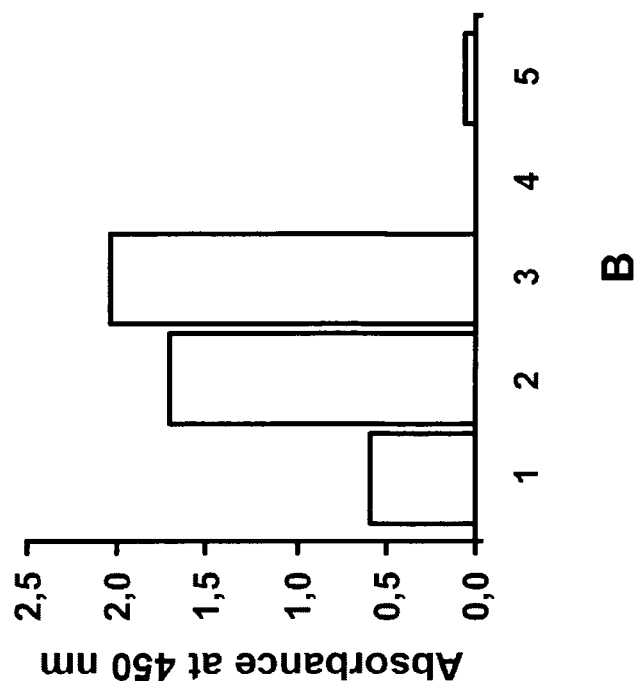
Figure 16:
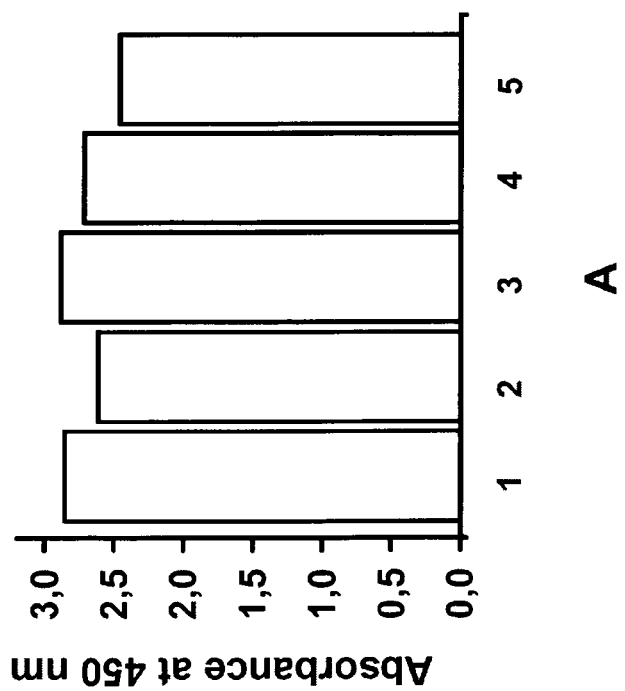

FIG. 16. A direct ELISA of the antibody 6E10 (panel A) and serum from hybridoma 20 expressing the monoclonal antibody mAb20 (panel B) against different forms of the Aβ$_{42}$-CC mutant. The 6E10 antibody recognizes the unstructured N-terminal of nearly all forms of Aβ. Antigen coated were (1) Aβ$_{42}$-CC monomers; (2) Aβ$_{42}$-CC monomers incubated at 37° C. and pH3.8 for 24 h; (3) Aβ$_{42}$-CC oligomers; (4) Aβ$_{42}$-CC oligomers treated with SDS; (5) Aβ$_{42}$-CC fibrils (reduced). MAb20 is specific for Aβ$_{42}$-CC oligomers, which are induced from monomeric Aβ$_{42}$-CC during incubation under acidic conditions (which promotes aggregation). The epitope is lost completely after SDS treatment.

Figure 17:
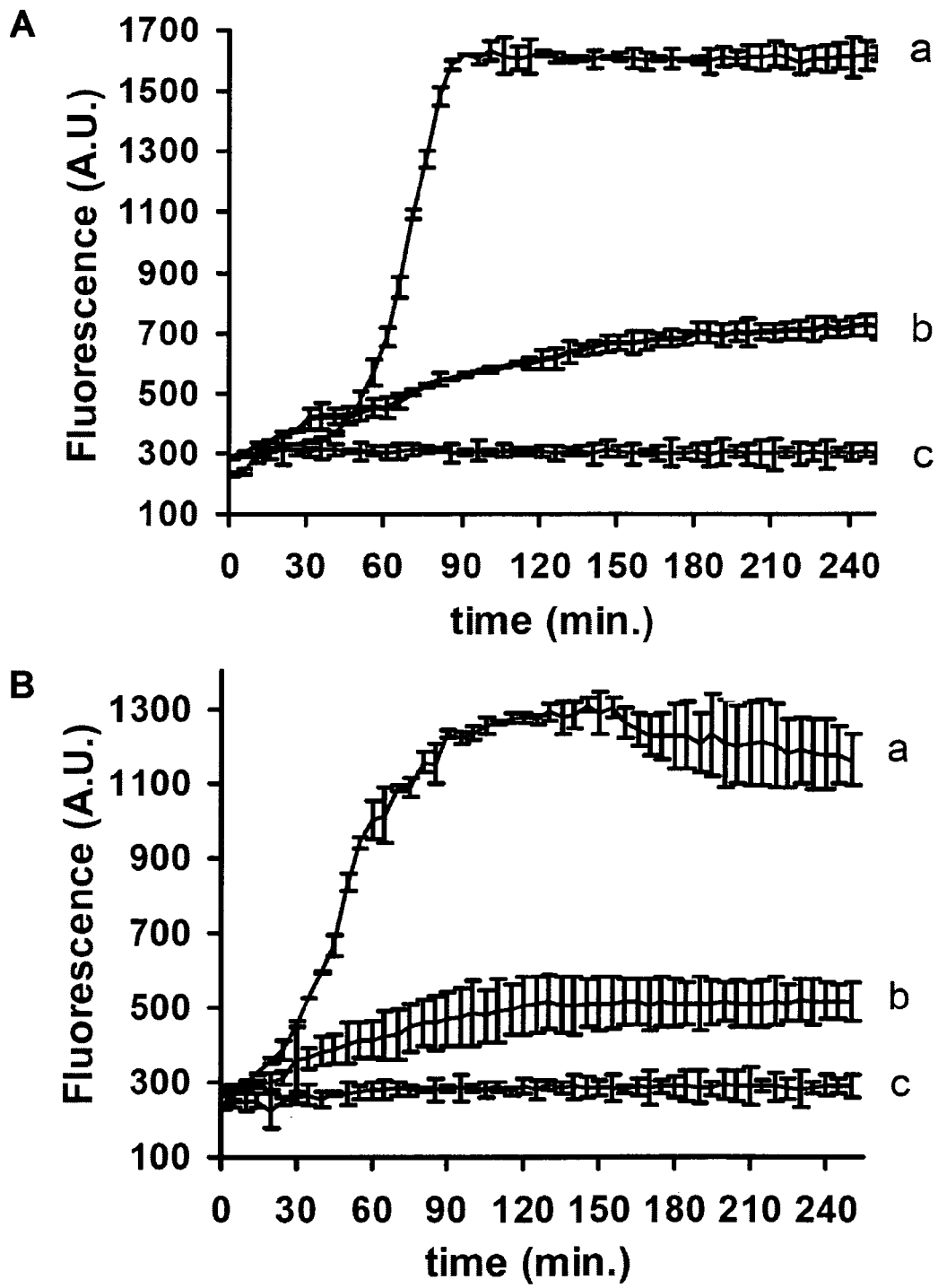

FIG. 17. Aggregation assays of (A) Aβ$_{42}$ and (B) Aβ$_{42}$ E22G (the Arctic mutation) in the absence (curves (a)) and presence (curves (b)) of purified mAb20. Baselines contained only mAb20 and Thioflavin-T (curves (c)). These assays monitor the fluorescence of Thioflavin-T as it binds to fibrils. Fibrillization is prevented by the presence of mAb20.

Figure 18:
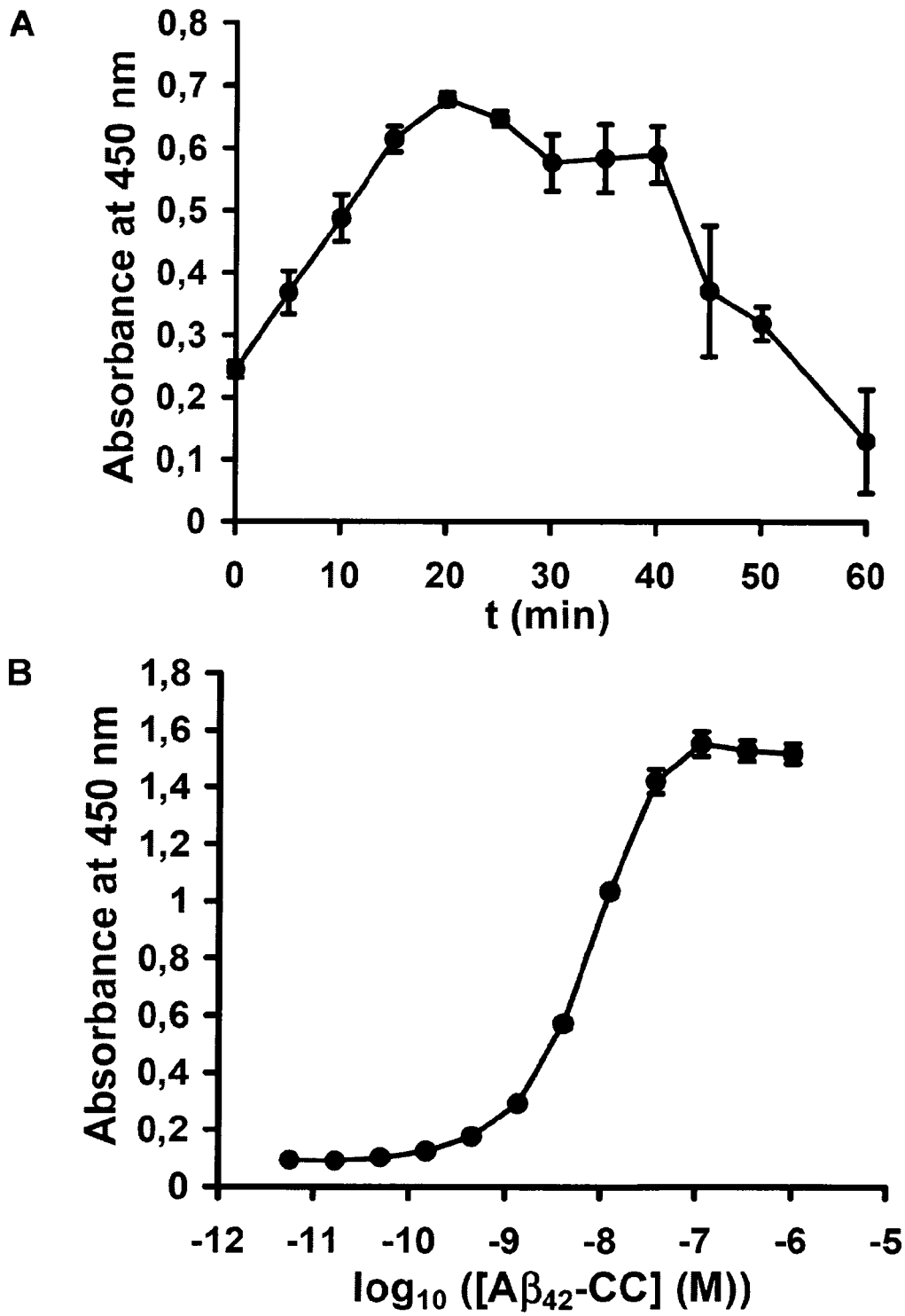

FIG. 18. A mAb20-mAb20 sandwich ELISA against Aβ$_{42}$ that was allowed to aggregate for 60 min. (A) Time samples were assayed and compared to (B) a standard curve obtained using Aβ$_{42}$-CC oligomers. MAb20 only binds to oligomers that are formed transiently before the onset of fibrillization. A maximum signal was obtained after 20 min, which corresponds to ~0.04% of the total Aβ present during aggregation.

Figure 19:
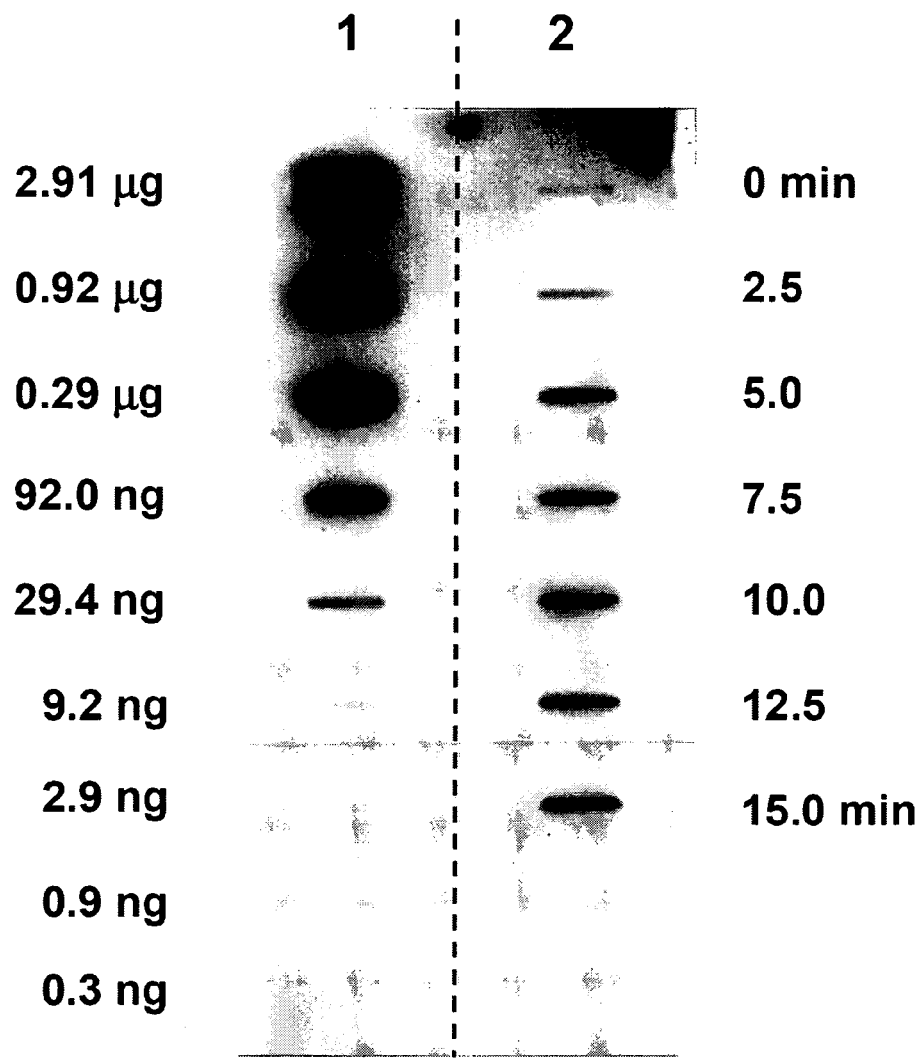
Figure 19:
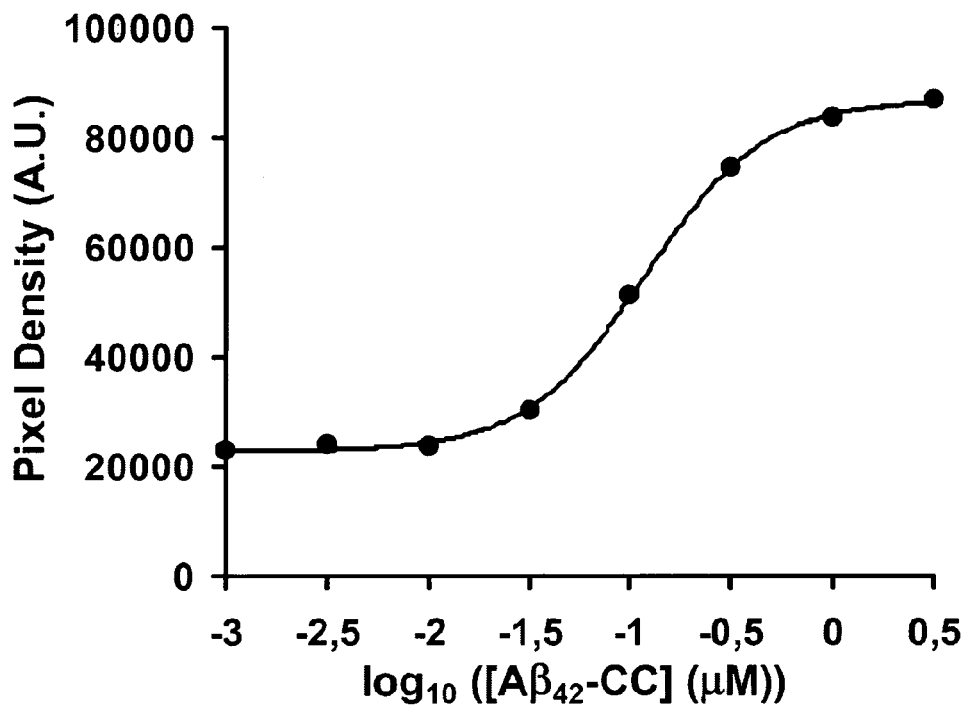
Figure 19:
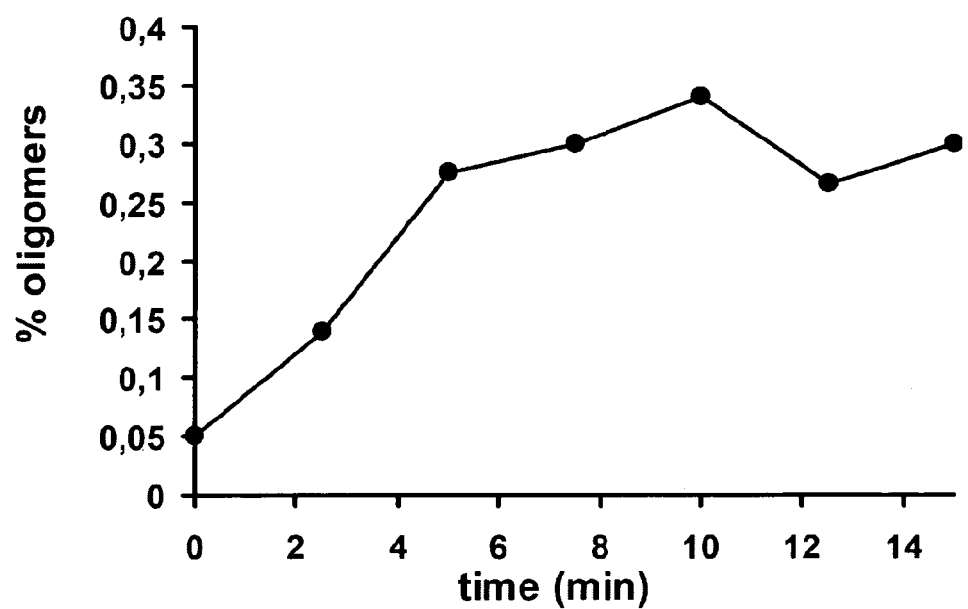

FIG. 19. (A) A slot blot experiment of aggregating Aβ$_{42}$ E22G (sample (2)) together with a standard curve obtained using Aβ$_{42}$-CC oligomers (sample (1)). The membrane was treated with purified mAb20 and the pixel densities of sample (1) were translated into (B) a standard curve, and sample (2) into (C) a quantification curve of the oligomers present during aggregation. A maximum oligomer signal is obtained after approximately 10 min, corresponding to slightly over 0.3% of the total Aβ$_{42}$ E22G present during aggregation.

Figure 20:
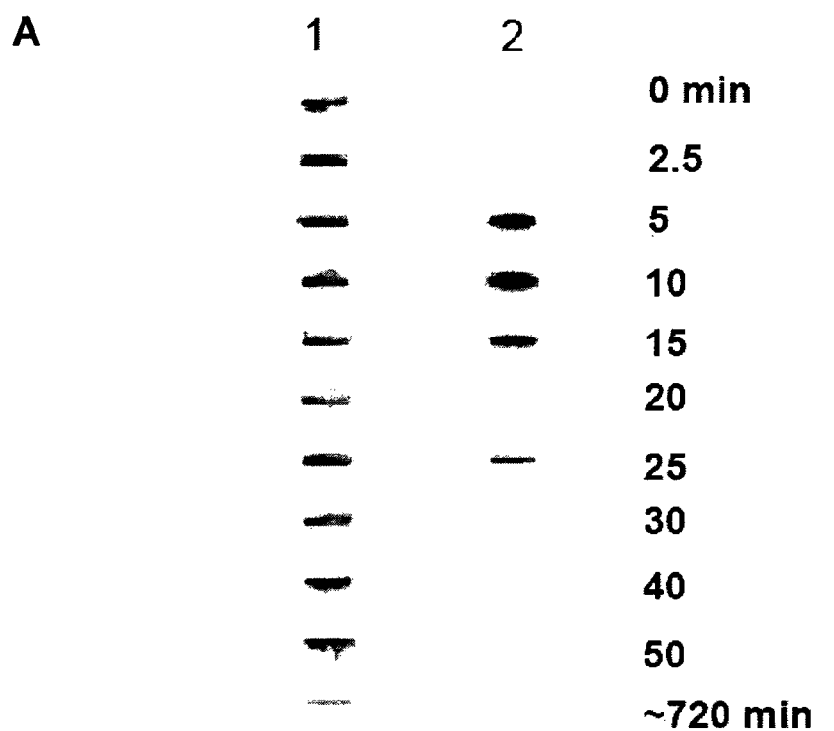
Figure 20:
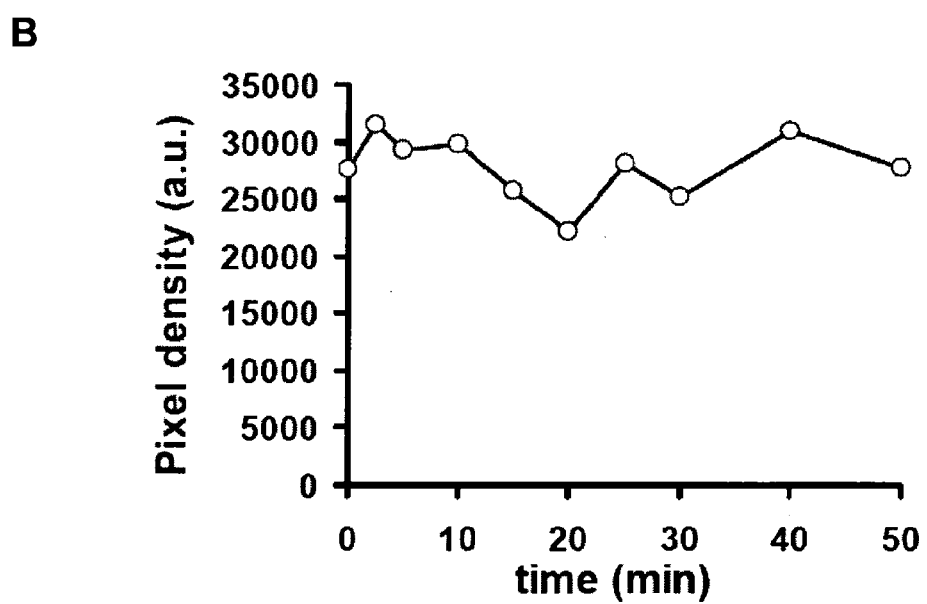
Figure 20:
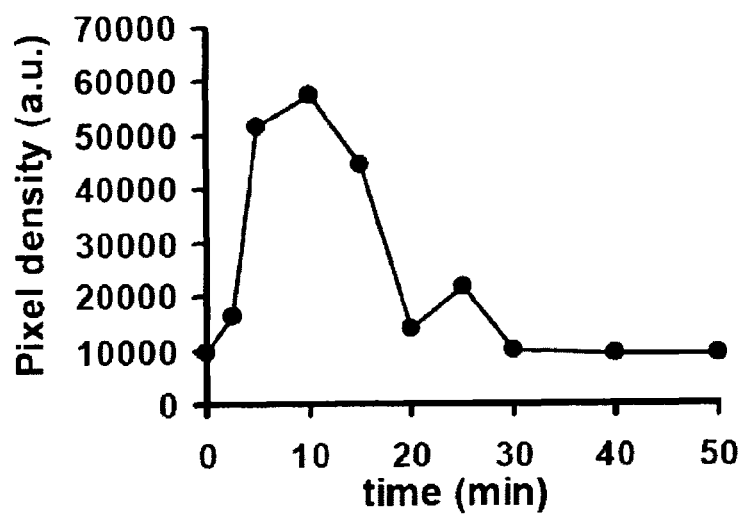
Figure 20:
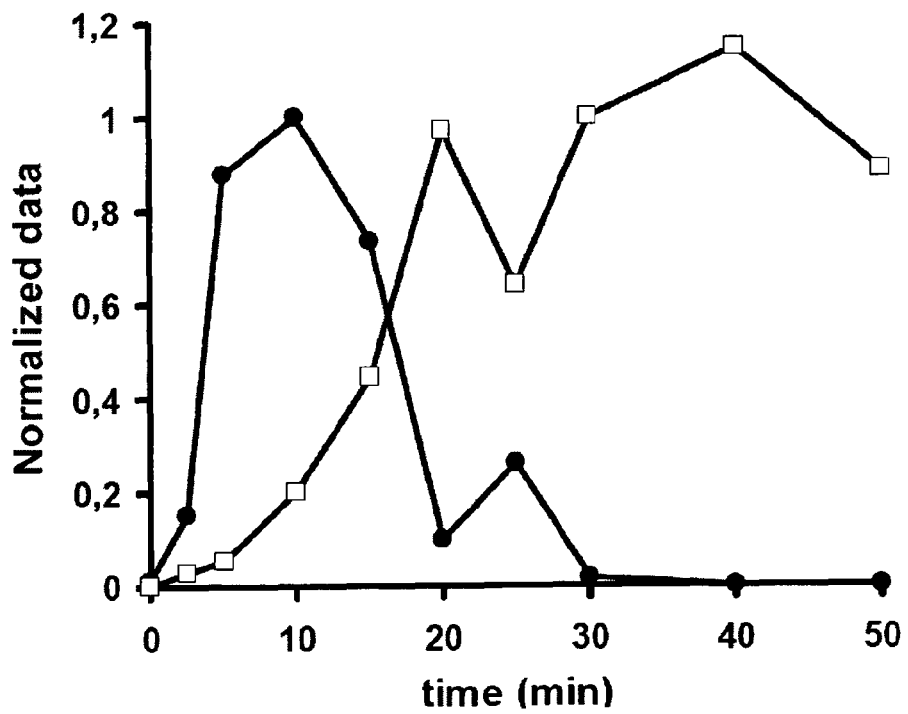

FIG. 20. An experiment on aggregating Aβ$_{42}$ E22G. Panel (A) shows a slot blot of the soluble material from time samples of aggregating Aβ$_{42}$ E22G. Samples were immobilized on two separate membranes, which were then treated with the 6E10 antibody (membrane 1) and purified mAb20 (membrane 2), respectively. (B) The pixel density of the signal from the 6E10 binding on membrane 1 is constant throughout the experiment. (C) The pixel density of the signal from mAb20 binding on membrane 2 increases sharply at the onset of the experiment, and then levels out to zero after 25-30 min. (D) A comparison of the mAb20-binding activity from membrane 2 and Thioflavin T-binding activity on insoluble material from the same aggregated samples. MAb20-binding occurs before insoluble fibrils are detected, and diminishes rapidly as the fibrils accumulate. This binding activity correlates well with the expected presence of oligomers. (-○-) The antibody 6E10; (-●-) mAb20; (-□-) Fluorescence of Thioflavin T on insoluble material.

DETAILED DESCRIPTION OF THE INVENTION

Amino Acid Sequence Identity

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:1 (the length of the sequence set forth in SEQ ID NO:1 is 10) and the number of matches is 9, then the sequence has a percent identity of 90% (i.e., 9÷10*100=90) to the sequence set forth in SEQ ID NO:1.

Antibodies

The term "antibody or antibody fragment" as referred to herein include whole antibodies and any antigen binding fragment referred to as "antigen-binding portion" or single chains thereof.

An "antibody" refers to a protein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

In the absence of structural data on the antibody-antigen complex, CDR regions are usually assigned according to Kabat or Chothia. Kabat derived CDR definitions from antibody sequence information alone (Kabat, E. A. et al. (1991) *Sequences of Proteins of Immunological Interest*, 5$^{th}$ Ed., National Insititutes of Health, Bethesda, Md., USA). The Chothia definitions, on the other hand, are based on threedimensional structures of antibodies and topologies of the CDR loops (Chothia, C., and Lesk A. M. (1987) *J. Mol. Biol.* 196:901; Chothia, C. et al. (1989) *Nature* 342:877). Herein, CDR sequences were assigned in accordance with the method used by the modelling algorithm AbM (Oxford Molecular), which was developed by Martin (Martin, A. C. et al. (1989) *Proc. Natl. Acad. Sci. USA* 86:9268). The AbM method is summarized at http://www.bioinf-org.uk/abs, and is a modified version of the Chothia definitions. According to the widely adopted Kabat residue numbering scheme of the variable antibody chains (Kabat, E. A. *Op. cit.*), the CDR's are thus assigned (according to AbM): VH-CDR1 26-35B, VH-CDR2 50-58, VH-CDR3 95-102, VL-CDR1 24-34, VL-CDR2 50-56, and VL-CDR3 89-97. Here, VH denotes "Variable Heavy" and VL "Variable Light" as described above.

The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fab' fragment, which is essentially an Fab with part of the hinge region; (iv) a Fd fragment consisting of the VH and CH1 domains; (v) a Fv fragment consisting of the VL and VH domains of a single arm of an antibody, (vi) a dAb fragment which consists of a VH domain; (vii) an isolated complementarity determining region (CDR); and (viii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Such single chain antibodies are also intended to be encompassed within the term "antigen-binding portion" of an antibody. Diabodies consists of two polypeptides each comprising a heavy (VH) chain variable domain connected to a light chain variable domain (VL) on the same polypeptide chain (VH-VL) connected by a peptide linker. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds Aβ is substantially free of antibodies that specifically bind antigens other than Aβ). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

Pharmaceutical Compositions

A pharmaceutical composition according to the invention may comprise a binding protein according to the invention in admixture with a pharmaceutically acceptable carrier and/or excipient, which will typically be selected with regard to the intended route of administration and standard pharmaceutical practice. The composition may be in the form of immediate-, delayed- or controlled-release applications. Preferably, the formulation is a unit dosage containing a daily dose or unit, daily sub-dose or an appropriate fraction thereof, of the active ingredient.

The pharmaceutical composition according to the invention may, or may not, be intended for, and, thus formulated in a manner suitable for, parenteral, intravenous, intra-arterial, intraperitoneal, intra-muscular, intracerebroventricular, or subcutaneous administration, or they may be administered by infusion techniques. They may be best used in the form of a sterile aqueous solution which may contain other substances, for example, enough salts or glucose to make the solution isotonic with blood or cerebral spinal fluid (CSF). The aqueous solutions may be suitably buffered (preferably to a pH of from 3 to 9), if necessary. The preparation of suitable pharmaceutical formulations under sterile conditions is readily accomplished by standard pharmaceutical techniques well-known to those skilled in the art.

Such formulations may include aqueous and non-aqueous sterile injection solutions which may contain anti-oxidants, buffers, bacteriostats and solutes which render the formulation isotonic with the blood or CSF of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

A therapeutically effective amount of a binding protein according to the invention for administration to a patient, such as a human patient, on the basis of a daily dosage level may be from 0.01 to 1000 mg of binding protein per adult (for example, from about 0.001 to 20 mg per kg of the patient's body weight, such as 0.01 to 10 mg/kg, for example greater than 0.1 mg/kg and less than 20, 10, 5, 4, 3 or 2 mg/kg, such as about 1 mg/kg), administered in single or divided doses.

The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

EXAMPLES

Example 1

Sample Preparation and Aβ$_{42}$-CC Oligomer Characteristics

This example provides data from experiments that demonstrates that the oligomers used for monoclonal antibody development (i) are very similar to oligomers formed by Aβ$_{42}$-WT and Aβ$_{42}$-E22G, (ii) are remarkably resistant towards fibrillogenesis, and (iii) that they give rise to a high amount of dimer and trimer bands during SDS-PAGE.

The Aβ$_{42}$ A21C/A30C (Aβ$_{42}$-CC) mutant (described in WO 2009/128772) is first denatured in 6-7 M guanidinium chloride in Tris buffer (20 mM Tris, 50 mM NaCl, pH 8.5) for at least 3 h at room temperature (21±0.5° C.). Oligomers are then obtained by size-exclusion chromatography (SEC) under native conditions in either phosphate buffer (50 mM of either Na$^+$- or K$^-$-phosphate, 50 mM NaCl, pH 7.2) or Tris buffer (10 mM Tris-HCl, 150 mM NaCl, pH 7.4). A11 prefibrillar oligomers with β-structure used herein eluted as proteins with an apparent molecular mass of approximately 100 kDa (FIG. 2A) on a Superdex 200 PG 16/60 column (GE Healthcare) calibrated using globular protein standards. They were concentrated with VIVASPIN 20 spin columns (Sartorius), and the concentration was determined by absorbance spectroscopy using an extinction coefficient of 2230 cm$^{-1}$ M$^{-1}$ for the difference in absorbance at 280 and 300 nm (an example is shown in FIG. 2B). The absorbance spectra typically do not display light-scattering artifacts in the middle ultraviolet region (<300 nm), which indicates that the oligomers maintain their structural integrity during the concentration step. Nevertheless, upon concentrating these oligomers they oligomerize further into larger structures in a modular fashion (Sandberg, A. et al. (2010) *Proc. Natl. Acad. Sci. USA* 107:15595-15600). The smallest prefibrillar oligomer with β-structure appears to correspond to a dodecamer, which is speculated by us to be a dimer of hexamers (i.e. a dimer of six stacked hairpins) and the modular unit can thus be either a dodecamer or a hexamer.

Figure 1:
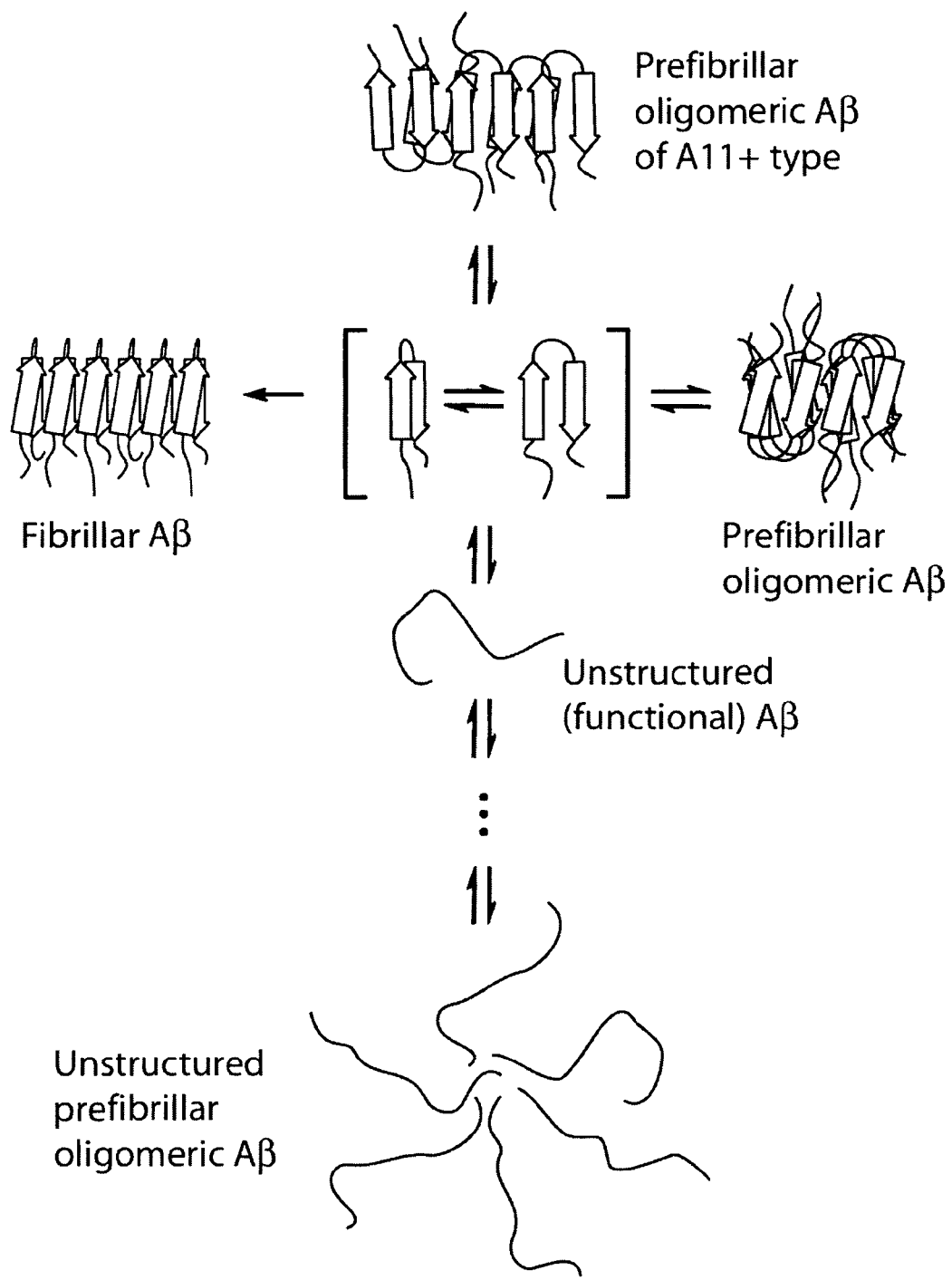
FIG. 1. One possible Aβ aggregation scheme displaying conformational changes conjectured to be associated with the different oligomers as the reaction inevitably proceeds towards the insoluble fibrillar end state.

Morphologically, the Aβ$_{42}$-CC oligomers used in this study resemble Aβ$_{42}$-WT oligomers and oligomers formed by the Aβ$_{42}$-E22G mutant. A transmission electron microscopy (TEM) micrograph (collected with a LEO 912 AB OMEGA electron microscope from Carl Zeiss SMT AG) of Aβ$_{42}$-CC oligomers is shown in FIG. 2C (the sample was applied to formvar/carbon coated Ni$^{2+}$ grids and negatively stained with 2% uranyl acetate; the scale bar is 0.2 μm). The aggregates all have a width of 6 nm, and variable lengths of up to ca. 35 nm. The smallest observable structures are circular with a diameter of 6 nm. These dimensions are also found in oligomers of Aβ$_{42}$-WT (see for instance FIG. 1C in Goldsbury, C. et al. (2005) *J. Mol. Biol.* 352:282-298) and are in agreement with what is expected for six repetitive hairpins stacked into a solenoid β-helix fold by hydrophobic interactions. Examples of such solenoid structures are the two choline-binding domains in the crystal structures of pneumococcal virulence factor LytA (1HCX.pdb; Fernàndez-Tornero, C. et al. (2001) *Nature Struct. Biol.* 8:1020-1024) and phage Cp-1 endolysin (1OBA.pdb; Hermoso, J. A. et al. (2003)

Structure 11:1239-1249). Both of these superhelical structures have a dimension of ~6 nm along the full helix (and a width of ~2.5 nm).

The oligomers produced by the A21C/A30C mutations are extremely resistant towards fibrillogenesis, which is demonstrated in FIG. 2D. Formation of fibrils was monitored by a Thioflavin-T (TFT) binding assay using a FLUOStar Optima reader (BMG) equipped with 440-nm excitation and 480-nm emission filters. The assays were carried out at 37° C. with orbital shaking between the data points. 50 mM Ktphosphate, 50 mM NaCl, supplemented with 10 μM TFT (pH 7.2) was used in this study. $A\beta_{42}$-CC oligomers were assayed at 100 μM concentration (referring to the equivalent monomer concentration). In two samples, 20 mM TCEP was added to break the disulfide bond and initiate fibrillogenesis, which is observed as a continuous increase in fluorescence as TFT binds to formed fibrils. However, oligomers stabilized by the disulfide bond remain intact during the course of the experiment, and fibrils are not formed. The baselines in FIG. 2D contained only buffer and TFT.

Figure 3:
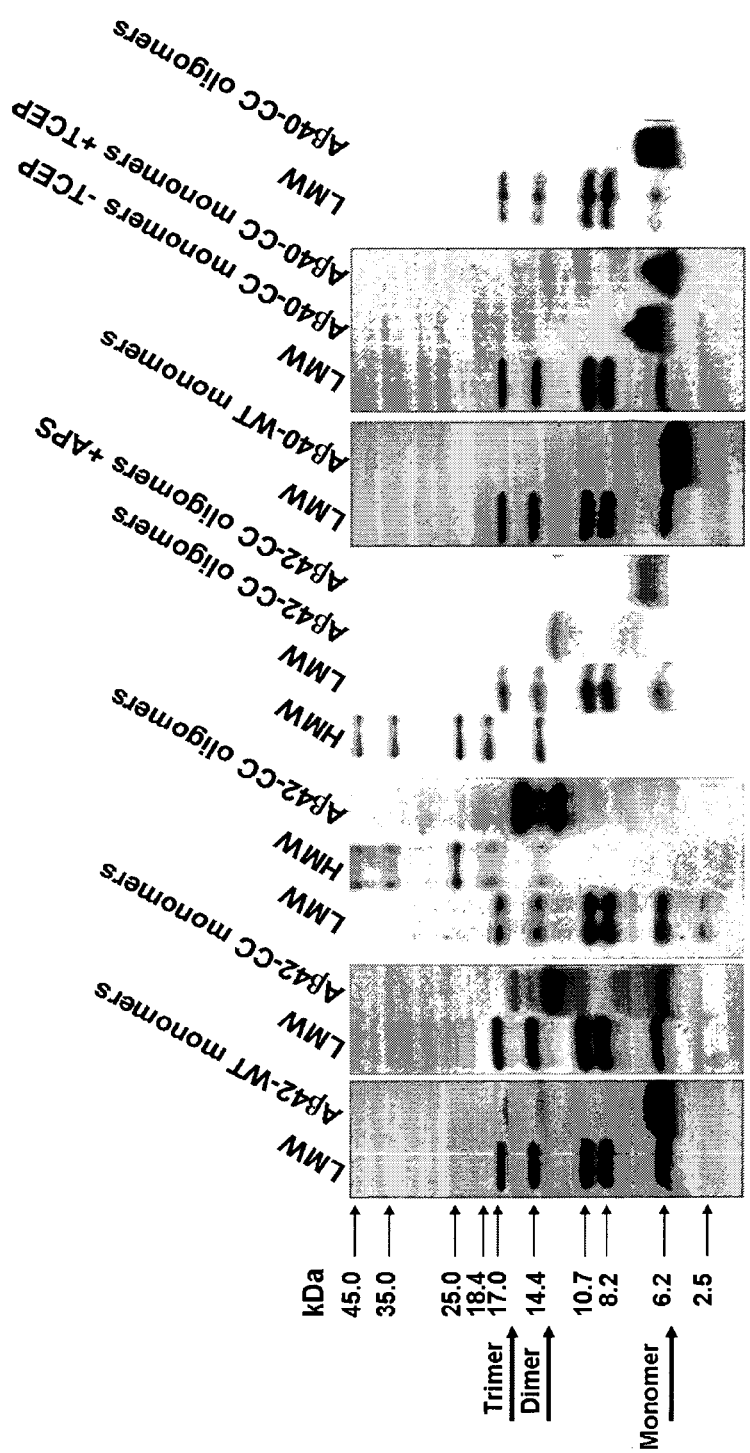
FIG. 3. SDS-PAGE of different Aβ derivatives. During SDS-PAGE the $A\beta_{42}$ variant always forms dimers and trimers, particularly so in the $A\beta_{42}$-CC mutant. In fact, the $A\beta_{42}$-CC oligomers migrate mainly as dimers. In contrast, all derivatives of the shorter (and less toxic) $A\beta_{40}$ variant only results in single monomeric bands. By including ammonium persulphate (APS) during the denaturation step in the presence of SDS the dimerization of $A\beta_{42}$ is effectively prevented. It is conjectured that this dimerization process is a chemical side reaction involving imides that form in the $A\beta_{42}$ oligomers as polar groups are desolvated upon oligomerization.

SDS-PAGE analysis (using 16.5% Tris-Tricine Criterion gels from Bio-Rad) of different Aβ species is shown in FIG. 3. The gels were stained with Coomassie. LMW refers to a low molecular weight protein standard, and HMW to a high molecular weight protein standard. In this figure, all samples were treated with reducing agent that breaks the disulfide bond (either β-mercaptoethanol or Tris-2-carboxyethylphosphine (TCEP)) except for one sample which is denoted "−TCEP". The band patterns of Aβ-CC derivatives is always the same whether reducing agent is included or not, which is to be expected if only intramolecular disulfide bonds have been formed. There are therefore no intermolecular disulfide bonds present in these different preparations of Aβ-CC derivatives.

The $A\beta_{42}$-CC oligomers used in the immunization trial exhibit the typical band pattern associated with toxic species of $A\beta_{42}$, namely the formation of a large number of dimeric and trimeric structures (FIG. 3). Note in FIG. 3 that $A\beta_{40}$ species do not form these dimers or trimers and, furthermore, that this shorter form of Aβ is not nearly as toxic as the 42 variant (for toxicity data, see: Sandberg, A. et al. (2010) Proc. Natl. Acad. Sci. USA 107:15595-15600). The high toxic effect of $A\beta_{42}$-CC oligomers thus seems to be coupled to the formation of multiple bands during SDS-PAGE. Furthermore, it has been shown previously that the appearance of dimer and trimer bands of Aβ in SDS-PAGE of brain samples correlates with aging and Alzheimer's disease phenotype (Enya, M. et al. (1999) Am. J. Pathol. 154:271-279; Shankar, G. M., et al. (2008) Nat. Med. 14:837-842). But it should be noted that dimers appear not to be toxic per se, but that they have been found to rapidly form stable and highly toxic protofibril-like oligomers (O'Nuallain, B. et al. (2010) J. Neurosci. 30:14411-14419).

Figure 4:
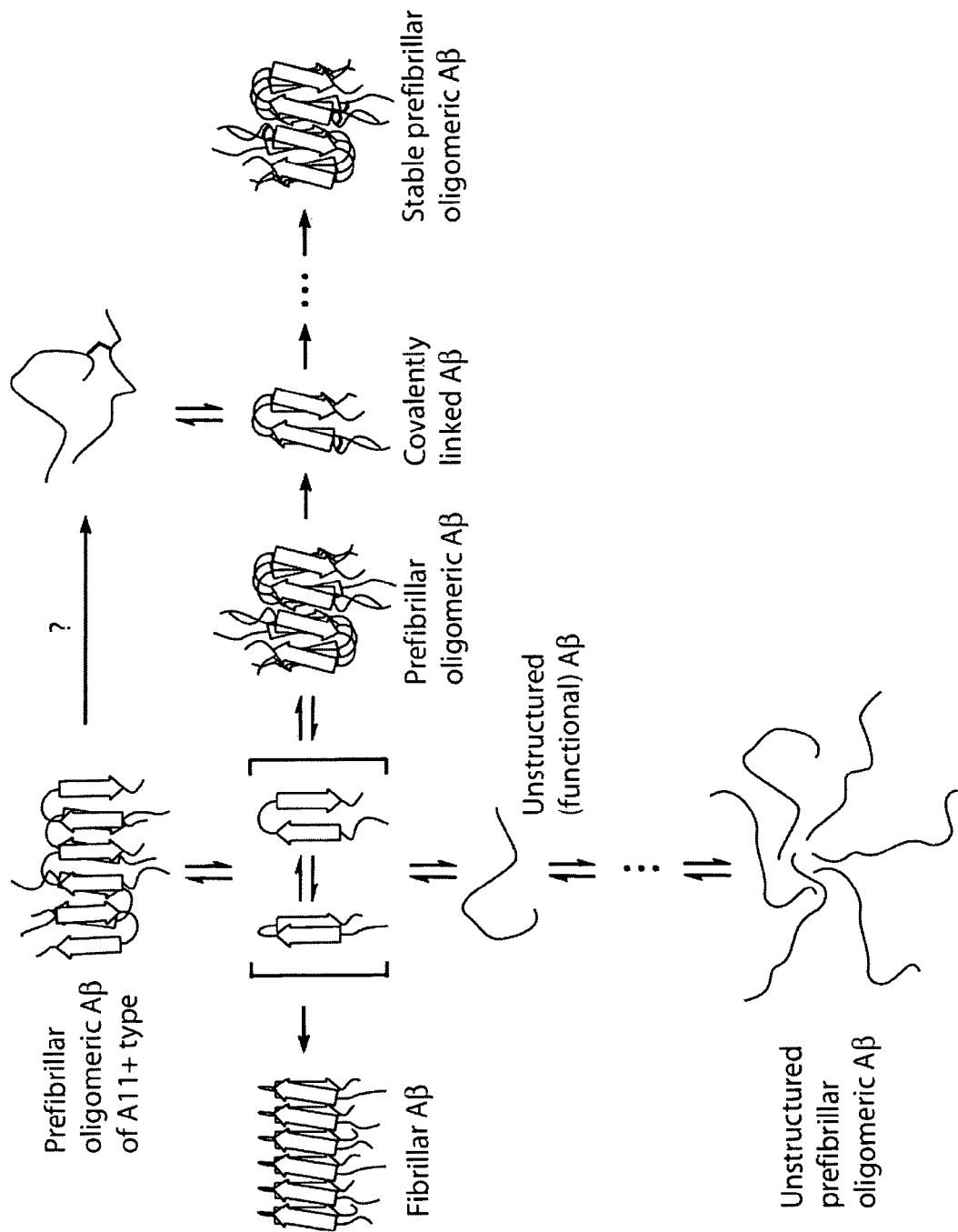
FIG. 4. A variant of the aggregation scheme depicted in FIG. 1 that also takes into account the irreversible linking step speculated to occur in $A\beta_{42}$ oligomers.

Without wishing to be bound by any theory, we hypothesize that the dimeric units observed in the brains of AD patients are a result of a chemical side reaction that occurs in the oligomers, and that causes Aβ peptides to attach covalently to each other. The covalent attachment of monomeric units will thermodynamically stabilize the toxic oligomeric forms (depicted in FIG. 4). One possible mechanism by which Aβ peptides may attach covalently is one whereby amines or other nucleophilic groups react with imide groups that form within the oligomers. It is conceivable that imides form as a result of desolvation of Asn, Gln, Asp, and/or Glu residues as aggregation proceeds. The result of a reaction between a primary amine and an imide is the formation of a stable amide bond between different Aβ peptides. A similar mechanism has been suggested for another dimerizing peptide (Severs, J. C. and Froland, W. A. (2008) J. Pharm. Sci. 97:1246-1256). Additional support also comes from the observation that a burst of $H_2O_2$ coincides with oligomer formation during the aggregation of Aβ when redox active ions are added (Tabner, B. J. et al. (2005) J. Biol. Chem. 280:35789-35792) and, conversely, that imides are formed when excessive $H_2O_2$ and redox active ions are added to solutions containing amides (Doumaux Jr., A. R. et al. (1969) J. Am. Chem. Soc. 91:3992-3993). Further support of the putative presence of imides in the oligomers comes from the previous observation of a large number of isomerized and racemized amino acids in the plaques isolated from actual Alzheimer's disease patients (Shapira, R. et al. (1988) J. Neurochem. 50:69-74), and it is well established that the intermediate in the reactions forming these derivatives involve imide formation (Geiger, T. and Clarke, S. (1987) J. Biol. Chem. 262:785-794). Moreover, we herein demonstrate that the dimerization reaction is effectively prevented by including ammonium persulphate (APS; a strong oxidizing agent) in the SDS-PAGE loading buffer (which was made of phosphate buffer). The sample denoted "+APS" in FIG. 3 was supplemented with 133 mM APS during heating, with the result that the $A\beta_{42}$-CC oligomers migrate exclusively as monomers. Without wishing to be bound by any theory, it is possible that APS outcompetes the nucleophile when SDS binding starts denaturing the oligomers and exposing desolvated imide groups.

We note that the specific structural factor, regardless of its constitution, that gives rise to the presence of these dimers and trimers during SDS-PAGE is also present in high amounts in the $A\beta_{42}$-CC oligomers used in the immunization study and the development of the monoclonal antibodies described in the examples below.

Example 2

The Immune Response in BALB/c and C56Bl/6 Mice Inoculated with $A\beta_{42}$-CC Oligomers Using Cholera Toxin (CT) as Adjuvant This example provides data that demonstrates that $A\beta_{42}$-CC oligomer immunization generates an immune response that contains a strong oligomer-specific IgG component and, furthermore, that these oligomer-specific antibodies do not react with monomers or fibrils. This observation was then exploited in Example 3 to specifically select hybridomas producing antibodies specifically reactive with oligomeric $A\beta_{42}$-CC and not reactive with monomeric $A\beta_{42}$-CC.

The immunization trial using the $A\beta_{42}$-CC oligomers was carried out as follows. The contents of each syringe were mixed in phosphate buffer saline (PBS; 20 mM Natphosphate, 150 mM NaCl, pH 7.4) immediately prior to inoculation to give a total volume of 200 μl. Five groups (or cohorts) of BALB/c mice, each group consisting of five individuals, received the following set of proteins injected into the peritoneum on day one:

1. 25 μg ovalbumin (Ova)+0.1 μg CT
 2. 25 μg Ova+100 μg $A\beta_{42}$-CC oligomers
 3. 25 μg Ova+0.1 μg CT+10 μg $A\beta_{42}$-CC oligomers
 4. 25 μg Ova+0.1 μg CT+100 μg $A\beta_{42}$-CC oligomers
 5. 0.1 μg CT+100 μg $A\beta_{42}$-CC oligomers.

One group of C57Bl/6, consisting of five individuals, was similarly inoculated with:

6. 25 μg Ova+0.1 μg CT+100 μg $A\beta_{42}$-CC oligomers.

After ten days, the above was repeated. None of the mice exhibited any abnormal activity or any other signs of detrimental effects during the full course of the experiment. After an additional eight days (i.e. on day 18), the mice were bled and sera were collected. A11 sera were stored at −24° C.

Ova is routinely used as an internal control that the immune system has responded accurately to the inoculation. It had no effect on the immune response towards $A\beta_{42}$-CC oligomers—no anti-$A\beta$ antibodies were found in group one, and no anti-Ova antibodies were found in group five.

Enzyme-linked immunosorbent assay (ELISA) of the sera was carried out in 96-well Maxisorp plates (Nunc). Each well was coated for 15 h at 4° C. with 100 μl of 2.2 μM solutions of antigen. After washing three times with PBS supplemented with 0.05% tween-20 (PBS-tween), plates were blocked with 150-200 μl 1% BSA in PBS at 37° C. for 30 min. Serum diluted 1:100 in PBS supplemented with 0.1% BSA was then added, and plates were incubated at room temperature (RT; 21±0.5° C.) for two hours. After washing three times with PBS-tween, a horseradish peroxidase (HRP) conjugated rat anti-mouse immunoglobulin (Ig) antibody (Southern Biotech) diluted in PBS with 0.1% BSA was added and plates were incubated for an additional 2 h at RT. After washing with PBS-tween as above, bound antibody was detected spectrophotometrically at 450 nm using 1 mg ml$^{-1}$ ortho-phenylenediamine (OPD; Sigma-Aldrich) as substrate in 100 mM Na$_3$-citrate-HCl buffer at pH 4.5 with 0.12‰ H$_2$O$_2$.

Antigens used were $A\beta_{42}$-CC oligomers and monomers prepared as described above (Example 1). One sample of monomers was made 20 mM TCEP and incubated at 37° C. and 800 rpm for 22 h to generate fibrils. Please note that this "fibril" sample probably also contains oligomers, as FIG. 2D demonstrates that the fibrillization reaction carried out at neutral pH is still ongoing after 22 h.

Figure 5:
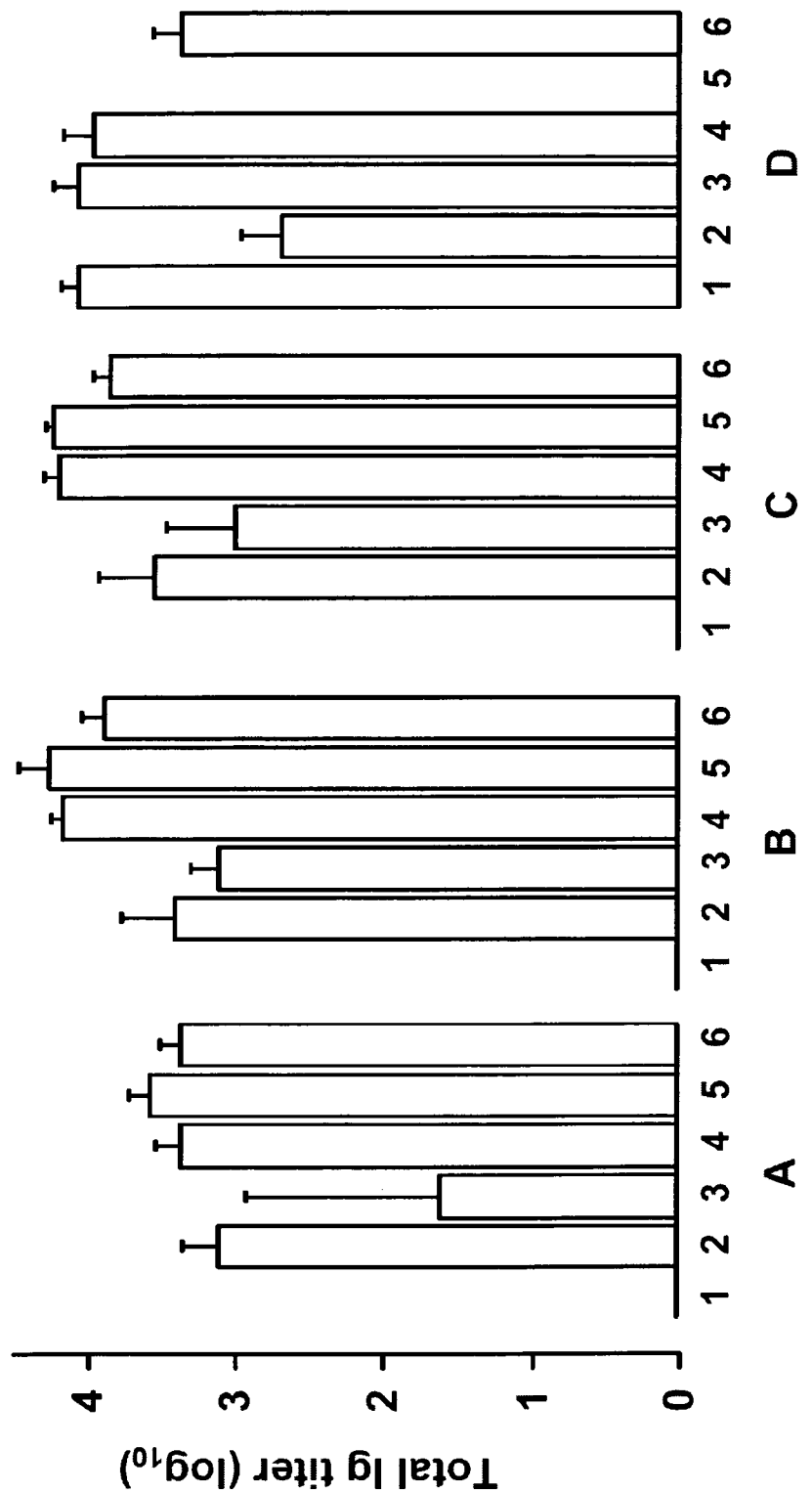
FIG. 5. Titers from a direct ELISA on polyclonal serum obtained by immunization using the oligomers presented in FIG. 2. Antigens coated were (A) $A\beta_{42}$-CC monomers, (B) $A\beta_{42}$-CC oligomers, (C) $A\beta_{42}$-CC fibrils, (D) Ovalbumin. Cohort (1) consisted of BALB/c mice immunized with 25 µg ovalbumin and 0.1 µg cholera toxin; Cohort (2) BALB/c mice immunized with 25 µg ovalbumin and 100 µg $A\beta_{42}$-CC oligomers; Cohort (3) BALB/c mice immunized with 25 µg ovalbumin, 0.1 µg cholera toxin, and 10 µg $A\beta_{42}$-CC oligomers; Cohort (4) BALB/c mice immunized with 25 µg ovalbumin, 0.1 µg cholera toxin, and 100 µg $A\beta_{42}$-CC oligomers; Cohort (5) BALB/c mice immunized with 0.1 µg cholera toxin and 100 µg $A\beta_{42}$-CC oligomers; Cohort (6) C57Bl/6 mice immunized with 25 µg ovalbumin, 0.1 µg cholera toxin, and 100 µg Aβ$_{42}$-CC oligomers.

This primary analysis of the sera is shown in FIG. 5. All mice within each group exhibited a similar immune response when immunized with $A\beta_{42}$-CC oligomers. Group three exhibited a weaker immune response towards $A\beta$ than the groups that received ten times more. When assaying this group (group three) against monomeric $A\beta_{42}$-CC two mice failed to reach signals required for accurate titer determination, and therefore the high standard error.

Clearly, FIG. 5 demonstrates that there is a strong immune response towards all forms of $A\beta$. Interestingly, however, there is a significantly larger amount of antibodies against oligomeric $A\beta$ compared to monomeric $A\beta$ in cohorts that received 100 μg $A\beta_{42}$-CC oligomers together with adjuvant (groups 4, 5, and 6).

To get a clearer view on the type of immune response that $A\beta_{42}$-CC oligomers invoke, serum was pretreated with fibrils in order to remove antibodies against the N-terminal (which is exposed in fibrils). A sample of 134 μM $A\beta_{40}$-CC monomers were first made 20 mM TCEP and incubated at 37° C. and 800 rpm for 3 days (this is fully sufficient for complete fibril formation). These were then centrifuged at 15 000×g for 40 min and the pellet washed once with PBS to remove any soluble non-fibrillated material. After centrifugation as above, the fibrils were resuspended in serum from cohort five (mice that received CT and $A\beta_{42}$-CC oligomers) diluted 1:200 in PBS with 0.1% BSA. The solution was incubated at 37° C. for 40 min and was during this period mixed by carefully inverting the tubes approximately every 5 min. After centrifugating as above the supernatant was used directly in an ELISA against $A\beta_{42}$-CC oligomers and monomers (the latter was made pH 10.4 in 50 mM Na$_2$CO$_3$, 50 mM NaCl, during immobilization in Maxisorp plates). Serum from cohort five diluted 1:200 was used as reference (untreated serum). The ELISA was carried out as above. The data is shown in FIG. 6, which demonstrates that fibril treatment removes anti-$A\beta$ antibodies against generic epitopes (such as the N-terminal, which usually dominates the immune response), but leaves a large amount of oligomer-specific anti-$A\beta$ in solution. It is clear from FIG. 6 that immunization with $A\beta_{42}$-CC generates an immune response that probably contains the usual response against the N-terminal of $A\beta$, but that this response also contains a very strong oligomer-specific component.

To further characterize the species to which these oligomer-specific antibodies bind, a dot-blot was performed on SEC fractions of $A\beta_{42}$-CC. The SEC profile is shown in FIG. 7A and the dot-blot to the fractions indicated in FIG. 7A is shown in FIG. 7B. In this experiment, Immobilion-P$^{SQ}$ membranes (Millipore) were used. Samples from the SEC were applied (scaled according to concentration) to two untreated membranes and allowed to air dry. These membranes were then blocked by overnight (15 h) incubation at 4° C. in a solution of 10% dry milk dissolved in 10 mM Tris-HCl buffer, pH 7.5, 150 mM NaCl, and 0.05% Tween-20 (TBST). Membranes were then washed three times for five minutes with TBST before addition of primary antibody solutions. These were prepared as follows: Polyclonal serum from cohort five was first diluted 1:100 in 500 μl PBS with 0.1% BSA containing 35 μM fibrils of both $A\beta_{40}$ and $A\beta_{42}$ (at a ratio of 3:1, respectively; the concentration refers to the monomers in the fibrils). After incubating at 37° C. for 1 h at 600 rpm, fibrils were removed by centrifugation at 15 000×g for 40 min (4° C.) leaving unbound antibodies in the supernatant. This supernatant (i.e. the fibril-treated serum) was then diluted to a total of 2 mL in TBST buffer with 5% dry milk and applied to one of the membranes. The other membrane was instead treated with the A11 polyclonal antibody solution (Biosource) at a concentration of 0.5 μg mL$^{-1}$ in TBST buffer with 5% dry milk. After incubating the membranes for 1 h at 21° C. under mild shaking, they were washed three times with TBST as above, and secondary antibody (HRP-conjugated goat anti-mouse IgG for the serum samples, and a HRP-conjugated goat anti-rabbit IgG for the A11 samples) diluted 1:2000 in TBST with 5% dry milk was added. After 1 h incubation as above, membranes were again washed and subsequently detected with a CCD camera and SuperSignal West Pico chemiluminescent substrate (ThermoScientfic).

The A11 polyclonal antibody solution recognizes a certain type of oligomer from several disease-associated proteins and peptides (Kayed, R. et al. (2003) Science 300:486-489). The arrow in FIG. 7B denotes where the sample of an A11 positive ("A11+") control solution of $A\beta$ was applied to each membrane. FIG. 7 demonstrates that the oligomers recognized by the oligomer-specific antibodies generated from $A\beta_{42}$-CC oligomer immunization are not the same oligomers that are recognized by the A11 serum. The A11+ aggregates typically elute in the void during SEC (WO 2009/128772; and also Sandberg, A. et al. (2010) Proc. Natl. Acad. Sci. USA 107: 15595-15600), and are hence usually very large structures.

In FIG. 8 a dot-blot experiment demonstrates that including monomeric (unstructured) $A\beta_{40}$-CC during binding of polyclonal serum to immobilized antigens has the same effect as pretreating the serum with fibrils and removing them with centrifugation. 5 μL 50 μM $A\beta_{42}$-CC monomers and oligomers obtained as in Example 1 (FIG. 2A) were blotted and allowed to dry on untreated Immobilion-P$^{SQ}$ membranes (Millipore). Membranes were blocked with 10% dry milk as above and treated with polyclonal serum. In this experiment serum from cohort 5 was diluted 1:600 in TBST with 5% dry milk. This solution was added to the top membrane, whereas the solution for the bottom membrane was first made 20 μM monomeric (unstructured) $A\beta_{40}$-CC and was incubated for 45 min under mild stirring at room temperature prior to application to the membrane. The rest of the protocol was carried out as above. From this experiment, presented in FIG. 8, it appears as if antibodies against the unstructured N-terminal are completely saturated by the excessive presence of $A\beta_{40}$-CC.

Consequently, all antibodies reactive with monomeric $A\beta_{42}$-CC also show reactivity with monomeric $A\beta_{40}$-CC. Antibodies specific for the C-terminal of $A\beta_{42}$ thus appears to be lacking.

FIG. 9 demonstrates that the oligomer-specific antibodies present in the polyclonal serum do not bind to fibrils, and it also shows that the $A\beta_{42}$-CC oligomers are extremely stable. Monomers and oligomers of $A\beta_{42}$-CC were obtained by SEC as in Example 1 (FIG. 2A). The shorter variant $A\beta_{40}$-CC only forms few oligomers with β-structure when denatured and subjected to SEC as in Example 1, and thus normally elutes from SEC mostly as unstructured low molecular-weight monomers and oligomers in the range 10 to 50 kDa (Sandberg, A. et al. (2010) *Proc. Natl. Acad. Sci. USA* 107:15595-15600). Nevertheless, 100 kDa oligomers are still obtained for $A\beta_{40}$-CC but in low amounts. In this experiment, 100 kDa oligomers from both $A\beta_{42}$-CC and $A\beta_{40}$-CC derivatives, as well as corresponding monomeric fractions, were first allowed to fibrillate by making 54-67 µM solutions 10 mM TCEP and incubating them at 1 000 rpm and 37° C. for 24 h, and then at 600 rpm and 37° C. for an additional 72 h, after which they were left standing at 21° C. for 16 h to further mature. It should be noted that TCEP is a stable reductant, unlike other reductants normally used to reduce disulfide bonds (such as β-mercaptoethanol and dithiothreitol (DTT)). These four solutions were then separated into insoluble (fibrillar) and soluble fractions by centrifugation at 15 000×g for 45 min. Supernatants were removed, and pellets resuspended in equal amounts of volume. 5 µL were then equally spotted on two different Immobilion-PFL membranes (Millipore) and allowed to air dry. In FIG. 9 soluble material was applied above the solid line, and insoluble material below the same line. Membranes were treated as above with respect to blocking and washing steps, and also with respect to the secondary antibody used and the method of detection. The right membrane in FIG. 9 was treated with serum containing 20 µM $A\beta_{40}$-CC monomers, whereas the left received untreated serum. This figure demonstrates that the oligomer-specific antibodies do not have affinity for fibrils, and that the $A\beta_{42}$-CC oligomers are remarkably stable even in the presence of 10 mM TCEP for extended periods of time. This is in analogy with FIG. 2D, where fibrillization is incomplete even after 40 h of shaking. The weak signal for insoluble $A\beta_{42}$-CC material on the right membrane in FIG. 9 is likely due to contaminating oligomers.

Example 3

Monoclonal Antibody Development from BALB/c Mice Inoculated with $A\beta_{42}$-CC Oligomers Using Complete and Incomplete Freund's Adjuvant (CFA and IFA, Respectively)

Six BALB/c mice were immunized according to the following schedule:
Day 0: CFA+100 µg $A\beta_{42}$-CC oligomers
Day 14: 75 µg $A\beta_{42}$-CC oligomers
Day 28: IFA+75 µg $A\beta_{42}$-CC oligomers
Day 42: 75 µg $A\beta_{42}$-CC oligomers
Day 56: IFA+75 µg $A\beta_{42}$-CC oligomers.

The immunological responses were analyzed by ELISA and dot-blots before proceeding with two mice for monoclonal antibody development. An example of a dot-blot experiment that demonstrates that these mice generated both a monomer and an oligomer-specific response is shown in FIG. 10. In this experiment the three mice that gave the highest titers in a direct ELISA against $A\beta_{42}$-CC oligomers (not shown) were assayed as follows: 5 µL of 20 µM solutions of both $A\beta_{40}$-CC and $A\beta_{42}$-CC oligomers and monomers were similarly blotted on two Immobilion-P$^{SQ}$ membranes and allowed to air dry. Membranes were blocked and washed as described above (see Example 2). Serum from the three mice was diluted 1:1000 in two identical solutions containing TBST with 5% dry milk, and one of these was also made 15 µM $A\beta_{40}$-CC monomers. The solutions with serum was added to the blocked and washed membranes and treated as described above. The result in FIG. 10 demonstrates that the immune response obtained from immunization with $A\beta_{42}$-CC oligomers with Freund's adjuvant contains an oligomer-specific component.

Two mice with the best titers in a direct ELISA against $A\beta_{42}$-CC oligomers were selected for fusion. They were boostered with 100 µg $A\beta_{42}$-CC oligomers. 72 hours later the mice were splenectomized.

Fusion was carried out as follows: Sp2/0 myeloma cells were cultured and diluted to 0.1 million cells per mL two days before fusion and used in growth phase. The spleen (in medium DMEM and 2% Pen/Strep), was transferred to a Petri dish and pressed through a sterile strainer to obtain splenocytes for the fusion. To the Petri dish, 10 mL medium was added (DMEM and 2% Pen/Strep) and cells and medium were collected and centrifuged for 5 minutes at 1 200 rpm. The pellet was resuspended, 1 mL Reed Blood cell lysis buffer was added and mixed one minute followed by addition of 20 mL medium and centrifugation 1 200 rpm for 7 min. At a ratio of 2:1 the splenocytes and Sp2/0 myeloma cells were mixed together in a tube with DMEM and 2% Pen/Strep and centrifuged 5 minutes at 1 200 rpm. The supernatant was discarded and pellet resuspended. The fusion was done according to standard procedures using polyethylene glycol and dimethyl sulfoxide (PEG/DMSO; Sigma-Aldrich) (for these procedures, please see: Harlow, E., and Lane, D., ed. *Antibodies: A Laboratory Manual*, Cold Spring Harbor, N.Y., (1998), p. 211-213; and: Davidson, R. L., and Gerald, P. S. (1977) *Methods Cell Biol.* 15:325-338). The cells were diluted in DMEM with addition of HAT media supplement (50×) hybri-Max™ (Sigma-Aldrich), 10% FBS (Gibco), 1 mM sodium pyruvate (100 mM, Lonza), 1% Pen/Strep, 10% condimed H1 hybridoma cloning supplement (Clone sup: Roche Diagnostics, Mannheim, Germany) and supernatant from SP2/0 cells (10%), giving 300 000 cells in 150 µL HAT medium in each well. Cells were then cultivated in 96 well clear flat bottom polystyrene tissue culture treated microplates (Microwell, Nunc) and incubated in a 5% $CO_2$ incubator at 37° C. with humified air. One week after fusion, HAT medium was exchanged.

Following two and three weeks post fusion, hybridoma supernatants were screened for monoclonal antibodies (mAb) against the selected antigen using ELISA. $A\beta_{42}$-CC oligomers were selected as antigen for positive selection, and $A\beta_{42}$-CC monomers were selected as antigen for counter selection. High binding 96 well plates (Maxisorp, Nunc) were coated with 2 µg/mL $A\beta_{42}$-CC oligomers in PBS and 2 µg/mL $A\beta_{42}$-CC monomers in $Na_2CO_3$ pH 10.4 (both antigens were coated on the same plate but in different wells) and stored at 4° C. over night. Blocking, to reduce unspecific binding, was done one hour at RT using blocking buffer (2% fat dry milk powder and 0.5% Tween-20 in PBS). Between each step the plates were washed three times using washing solution (1% NaCl and 0.05% Tween-20 in ddH$_2$O). Supernatant from selected clones was added at 1:5 dilutions with incubation buffer (IB; 0.05% Tween-20 in PBS) to the wells and incubated for two hours at RT. Secondary antibody GAM-HRP (Goat Anti-Mouse IgG(H+L) HRP-conjugate, BioRad) was diluted 1:2000 in IB and incubated one hour at RT. Clones positive for Aβ were visualized using EC-blue substrate (EC-blue enhanced, Medicago). The reaction was stopped using 0.5M H$_2$SO$_4$ and the plates were analyzed in a spectrophotometer at 450 nm.

Of approximately 60 stable Aβ positive clones, three were positive for Aβ$_{42}$-CC oligomers but negative for Aβ$_{42}$-CC monomers. These were selected and expanded to 48 well plates in HT$^+$ medium consisting of DMEM, 10% FBS, 10% Fetal clone serum (FC; HyClone Laboratories, Logan, Utah, USA), 10% clone sup, 1 mM sodium pyruvate, 1% PenStrep and HT supplement (50×) (hypoxanthine & thymidine, Gibco). The cells were then expanded further when confluent, changing the medium to 10% FBS (DMEM, 10% FBS, 1% Pen/Strep and 1 mM sodium pyruvate). Selected positive clones were frozen and stored in liquid nitrogen and/or −150° C. freezer according to standard cell-freezing protocols. Selected clones were subcloned by limited dilution.

Clones selected for expansion and purification were thawed according to standard thawing protocols and cultured in 10% FBS. For adaptation to SFM (SFM4 mAb, Hyclone), the cells were cultured in media consisting of 50% SFM (SFM and 0.2% Pen/Strep) and 50% medium with 10% FBS until confluent and the medium was then changed to 100% SFM.

The three positive clones selected were isotyped using IsoQuick™ Strips for Mouse Monoclonal Isotyping (Sigma-Aldrich). Clone #20 (mAb20) was isotyped as IgG3, whereas clones #50 and #56 were both isotyped as IgM. Clone #56 did not show any positive signal after subcloning and was therefore not characterized further. Clone #20 was ultimately chosen as it exhibited higher oligomer specificity than clone #50 and, furthermore, that it is of the IgG isotype.

Out of 10 subclones of mAb20 (all exhibiting consistency with respect to antigen specificity), one was chosen for expansion and purification. MAb20 was purified by Protein A chromatography (Ey, P. L., et al. (1978) *Immunochem.* 15:429-436).

Sequencing of the mAb20 gene in the hybridomas producing the antibody was done using standard techniques and protocols (Agrisera, Vännäs, Sweden). The DNA sequence encoding the variable heavy (VH) domain is shown as SEQ ID NO:7, the DNA sequence encoding the variable light (VL) domain is shown as SEQ ID NO:9. The corresponding deduced amino acid sequences are shown as SEQ ID NO:8 and SEQ ID NO:10, respectively.

N-terminal sequencing of purified mAb20 was done in order to verify that the correct gene had been sequenced.

Example 4

Characterization of the Oligomer-Specific Monoclonal Antibody 20 (mAb20) Against Aβ-CC Derivatives This example provides data that demonstrates that mAb20 is very specific for Aβ$_{42}$-CC oligomers, and that is does not recognize unstructured (monomeric) or fibrillar forms of Aβ.

Serum from mAb20-producing hybridomas was assayed against Aβ-CC derivatives in a direct ELISA. Monomers and oligomers of both Aβ$_{40}$-CC and Aβ$_{42}$-CC (obtained as in Example 1) were immobilized on Maxisorp plates (Nunc) and the ELISA carried out as in Example 2 but instead using an alkaline phosphatase-conjugated rabbit anti-mouse Ig antibody (Dako) and 4-nitrophenyl phosphate (NPP) as substrate. The monoclonal antibody 6E10 (Covance Research Products), which recognizes the amino acids 3-8 in the N-terminal of Aβ, was used as reference (diluted to 1 μg mL$^{-1}$). The kinetic traces (recorded as absorbance at 405 nm) are shown in FIG. 11. In this figure there is also signal developing for mAb20 when using Aβ$_{42}$-CC monomers as antigen. However, this is most likely the result of the mAb20 antibody binding to a subpopulation of antigen, and not low affinity interaction with monomers in general, as the titers from a 3-fold dilution ELISA series (8 dilutions) are similar for both antigens (FIG. 12). This is also in line with the data presented in FIG. 13, which presents an ELISA where monomeric Aβ$_{42}$-CC was allowed to bind to the Maxisorp plates under different conditions: at pH 7.4, at pH 10.4, and at pH 10.4 in the presence of 10 mM TCEP (all three at 4° C. for 13 h). It is known that high pH helps maintain Aβ peptides in unstructured form in solution (Fezoui, Y. et al. (2000) Amyloid 7:166-178). High pH thus prevents aggregation/oligomerization during the immobilization step, and there is indeed less signal developing for mAb20 (but not for 6E10) in the samples that were allowed to bind under high-pH conditions. The titers, however, were nearly identical in all samples for both 6E10 and mAb20: total Ig titer (log$_{10}$) at pH 7.4 was 2.8 for mAb20 and 2.1 for 6E10; total Ig titer at pH 10.4 was 2.9 for mAb20 and 2.0 for 6E10; total Ig titer at pH 10.4 with 10 mM TCEP was 3.0 for mAb20 and 2.1 for 6E10.

The data in FIGS. 11 and 12 thus demonstrate that mAb20 has virtually no affinity for monomeric and oligomeric forms of Aβ$_{40}$-CC, but high affinity for Aβ$_{42}$-CC oligomers and a subpopulation of Aβ$_{42}$-CC monomers. It is plausible that this subpopulation consists of peptides that has oligomerized during the course of the experiment. Alternatively, it is possible that this signal results from a subset of monomers populating a specific (aggregation prone) conformation.

To assay the affinity of mAb20 for fibrils, Aβ$_{40}$-CC and Aβ$_{42}$-CC were first treated with 10 mM TCEP and allowed to fibrillate by incubating them at 1 000 rpm and 37° C. for 24 h, and then at 600 rpm and 37° C. for an additional 72 h, after which they were left standing at 21° C. for several weeks. Before analysis, insoluble (fibrillar) and soluble fractions were separated by centrifugation at 20 000×g for 15 min. Supernatants were removed, and pellets resuspended in an equal amount of volume. Maxisorp plates (Nunc) were coated with the fibrils as in Example 2 and the ELISA carried out as above using the same alkaline phosphatase-conjugated rabbit anti-mouse Ig antibody (Dako) for detection. FIG. 14 shows the kinetics of the appearing absorbance at 405 nm, and FIG. 15 shows the calculated titers from a 3-fold dilution ELISA series (8 dilutions) for each time point. No absorbance appeared for the mAb20 antibody, whereas the control antibody 6E10 recognized both fibril samples with titers comparable to the other Aβ$_{40}$-CC and Aβ$_{42}$-CC derivatives presented above.

FIG. 16 presents data from an experiment that demonstrates that the mAb20 epitope in Aβ$_{42}$-CC oligomers is completely lost after SDS treatment, but that it appears in monomer samples of Aβ$_{42}$-CC after incubation under acidic conditions. This ELISA experiment was carried out as above using a HRP-conjugated sheep anti-mouse IgG as secondary antibody (Amersham) and OPD as substrate. The 6E10 antibody was used as reference. The samples of Aβ$_{42}$-CC were treated as follows: Two solutions of 50 μM monomers were incubated in 10 mM HCl (pH 3.55±0.25) at 600 rpm and 37° C. for 24 h—one without TCEP, and one with 10 mM TCEP to break the disulfide bond and initiate fibril formation. These were then diluted to 1.1 µM with PBS (pH 7.4) before being added to the Maxisorp plates. Furthermore, a 50 µM oligomer sample was made 2% SDS in PBS and heated at 95° C. for 5 min, allowed to cool down to RT, and was then diluted in 50 mM $Na_2CO_3$ buffer, 50 mM NaCl (pH 10.4) before being added to the Maxisorp plate. The plate with the acid-treated samples and reference samples of $A\beta_{42}$-CC oligomers and monomers were coated at 4° C. for 15 h, whereas the plate with SDS-treated samples was sealed and coated at 37° C. for 1 h (to prevent precipitation of SDS).

Aβ aggregation in general exhibits a strong dependence on pH, and acidic pH is often used to accelerate fibril formation (e.g. Stine, W. B. et al. (2003) *J. Biol. Chem.* 278:11612-11622). However, incubating $A\beta_{42}$-CC monomers in 10 mM HCl at 600 rpm and 37° C. for 24 h does not produce fibrils, but it does produce oligomers that bind mAb20 (FIG. 16). This is yet further testament to the remarkable stability of the $A\beta_{42}$-CC oligomers. It is also interesting that the epitope is lost completely after SDS treatment. This demonstrates that the mAb20 epitope is specific for native oligomers, but not for denatured oligomers that (presumably) contains a high proportion of unstructured dimers (cf. SDS-PAGE data in FIG. 3).

Example 5

Characterization of the Oligomer-Specific Monoclonal Antibody 20 (mAb20) Against $A\beta_{42}$-WT and $A\beta_{42}$-E22G Derivatives This example provides data from experiments that demonstrates that mAb20 also recognizes $A\beta_{42}$-WT and $A\beta_{42}$-E22G oligomers, and that it binds specifically to soluble species that form transiently during the aggregation process before the appearance of fibrils.

Wild-type and the E22G mutant (the Arctic mutation) of $A\beta_{42}$ were prepared as in Example 1, but with the following important exception: During the SEC, the pH of the buffer was raised to 10.4-10.7 in order to keep these aggregation-prone derivatives in their unstructured monomeric states. This step is thus carried out at a pH where the buffer (phosphate or Tris) is in its unbuffering region. Despite this, control measurements indicated that the pH remained stable at 10.4-10.7 throughout the SEC run and also during the limited storage of the obtained solutions (which were kept in sealed tubes on ice or at 4° C.). The E22G derivative was prepared fresh before each experiment and used within 6 h, whereas the wild-type peptide was used within 24 h. Immediately prior to analysis, the pH of the solutions containing eluted monomers was lowered to 7.2-7.4 by careful addition of HCl.

Aggregation assays were performed on monomeric $A\beta_{42}$-WT and $A\beta_{42}$-E22G in the presence and absence of mAb20. The E22G mutation (also known as the Arctic mutation) is associated with familial Alzheimer's disease and is known to cause Aβ peptides to rapidly aggregate into toxic structures (Nilsberth, C. et al. (2001) *Nat. Neurosci.* 4:887-893). In this experiment, the concentration of peptide and mAb20 was 15 µM and 2 µM, respectively. MAb20 concentration was estimated from the absorbance at 280 nm where 1.0 mg ml$^{-1}$ was assumed to have an absorbance of 1.36, and from the assumption that IgG3 antibodies typically have a molecular weight of 170 kDa (which was confirmed by SDS-PAGE; not shown). Thioflavin-T (TFT) was added to 10 µM and NaCl to 150 mM. Tris was used as buffer at a concentration of 10 mM and the pH was adjusted to 7.4. Aggregation assays were performed using a FLUOStar Optima reader (BMG) equipped with 440-nm excitation and 480-nm emission filters. The assays were carried out at 37° C. with orbital shaking between the data points. FIG. 17A shows the result for $A\beta_{42}$-WT with and without mAb20, and FIG. 17B for $A\beta_{42}$-E22G with and without mAb20. The average data from two different runs with standard errors are shown. Solutions containing only mAb20 are also shown.

FIG. 17 demonstrates that mAb20 prevents fibrillization of $A\beta_{42}$ WT and E22G derivatives, both which are normally known to undergo rapid fibrillogenesis under these conditions (physiological ionic strength, 37° C., and with shaking).

A sandwich-ELISA protocol was established using mAb20 for capture and biotinylated mAb20 for detection together with HRP-conjugated Streptavidin (R&D Systems). MAb20 was biotinylated with the EZ-Link sulfo-NHS-biotin kit (Thermo Scientific) according to the manufacturer's instructions. Maxisorp plates (Nunc) were coated with 240 ng mAb20 at 4° C. for 15 h, washed three times with PBS-tween, and was then blocked with 1% BSA in PBS at RT for 1 h. After removal of the blocking solution, plates were treated with antigen (see next section) for 2 h at RT and were then washed as above. Approximately 350 ng biotinylated mAb20 in PBS with 0.1% BSA was then allowed to equilibrate with captured antigen for 1 h at RT. After washing as above, the HRP-conjugated Streptavidin solution in PBS with 0.1% BSA was added at the dilution recommended by the manufacturer (1:200) and the plates incubated for an additional hour at RT. Washing as above removed unbound HRP-Streptavidin, and bound enzyme was detected spectrophotometrically at 450 nm using 1 mg ml$^{-1}$ OPD substrate in 100 mM $Na_3$-citrate-HCl buffer at pH 4.5 with 0.12‰ $H_2O_2$.

Antigen was prepared as follows: Twelve 100-µl samples of monomeric $A\beta_{42}$-WT (prepared under high-pH conditions) at 20 µM in 10 mM Tris-HCl, 150 mM NaCl, pH 7.4 were allowed to aggregate at 37° C. and 600 rpm for 0, 2.5, 5, 10, 15, 20, 25, 30, 45, and 60 min. This experiment started with the aggregation of the 60 min sample, and all other samples were incubated on ice until it was time to start the aggregation (the 45 min sample, for example, was thus incubated on ice for 15 min before commencement of the aggregation assay). Incubating on ice prevents aggregation. With this protocol, all samples reached the end of their respective aggregation times at the same time, at which point they were allowed to cool on ice for 5 min. They were then diluted with 1% BSA to give a final concentration of 0.1% BSA, and were added to the mAb20-coated and BSA-blocked Maxisorp plates and the sandwich-ELISA subsequently carried out as described in the previous section. The data from two similar experiments is presented in FIG. 18A. In addition, a standard curve with $A\beta_{42}$-CC oligomers was obtained from a parallel sandwich-ELISA experiment, which allows for a rough quantitation of the amount of wild-type oligomers present at a given time point during the aggregation process. The data from a set of two reference curves is shown in FIG. 18B (where the concentration refers to the equivalent concentration of monomers). It is clear that mAb20-binding occurs at the onset of aggregation, but diminishes as aggregation proceeds. At 20 min, the absorbance corresponds to 5.5-7.7 nM detected $A\beta_{42}$-CC oligomers which would indicate that there is a maximum of only ~0.04% $A\beta_{42}$-WT oligomers present during the aggregation. This is not surprising considering that the conditions under which aggregation was allowed to proceed strongly promotes aggregation, and is thus a reflection of the dynamic process of aggregation where the transiently populated oligomers continuously form the stable fibrillar end state. This is also in accordance with the recent finding that less than 1% proper oligomers could be detected in preparations (i.e. "enrichments") of oligomers of Aβ$_{42}$ that followed a standard protocol encompassing incubating peptides in F12 culture medium at 4° C. over night (Fukumoto, H., et al. (2010) *FASEB J.* 24:2716-2726).

A similar quantitation of oligomers was performed on actively aggregating Aβ$_{42}$-E22G using a slot-blot protocol. Monomeric Aβ$_{42}$-E22G was prepared in 10 mM Tris, 150 mM NaCl at high pH (10.7) as above, and used within hours of elution from the SEC column. The concentration of peptide was 20 µM, and the pH was adjusted to 7.4 immediately prior to commencement of the aggregation assay. Samples of 200 µl peptide solutions were aggregated at 37° C. and 600 rpm for different amounts of time: 0, 2.5, 5, 7.5, 10, 12.5, and 15 min. All samples were kept on ice up until the start of the aggregation assay (as above), and were also cooled on ice for 5 min after completion of the assay. Insoluble aggregates were removed by centrifugation at 20000×g and 4° C. for 10 min. Soluble material was applied to a Immobilion PFL membrane (Millipore) using a PR 648 slot blot manifold (Amersham Biosciences). A reference curve of Aβ$_{42}$-CC was prepared by similarly applying samples at a concentration ranging from 3.16 µM to 0.31 nM to the membrane (note that these concentrations refer to monomeric Aβ, but that this sample nevertheless contains virtually 100% oligomers). The membrane was then treated as previously described (see the dot blotting procedures described above) using mAb20 at 1.2 µg ml$^{-1}$ as primary antibody and a HRP-conjugated anti-mouse IgG from sheep (Amersham Biosciences) as secondary antibody. SuperSignal West Femto chemiluminescent substrate (Thermo Scientific) was used for detection. The membrane is shown in FIG. 19A. Bio-Rad's software Quantity One was used to obtain the pixel density for each point.

The obtained reference curve for Aβ$_{42}$-CC is shown in FIG. 19B. The amount of oligomers present during actively aggregating Aβ$_{42}$-E22G, shown in FIG. 19C, was calculated based on the reference curve. The amount of oligomers reaches a maximum of 0.34% after 10 min of aggregation, which is 8.5 times as many as for actively aggregating Aβ$_{42}$-WT peptide. This is in accord with the view that the E22G mutation stabilizes the toxic conformation in the oligomers, thereby causing the aggravated disease phenotype observed in familial cases of Alzheimer's disease that carry the mutation.

A similar slot blot procedure of aggregating Aβ$_{42}$-E22G is shown in FIG. 20. This experiment monitored the aggregation process for a longer period of time and also examined concomitant fibril formation. Solutions containing 20 µM Aβ$_{42}$-E22G in 10 mM Tris-HCl, 150 mM NaCl, pH 7.2, was aggregated as above for 0, 2.5, 5, 10, 15, 20, 25, 30, 40, and 50 min. (A reference sample containing fully fibrillated material obtained after 720 min was also analyzed.) After being cooled on ice for 5 min, 500 µl was centrifuged as above and 250 µl was applied to two different Immobilion PFL membranes using the slot blot manifold. Both membranes were treated as above but with different primary antibodies: one membrane was treated with mAb20 and the other membrane with the 6E10 antibody at 1 µg ml$^{-1}$. The 6E10 recognizes all types of Aβ by binding to the N-terminal. The membranes and the pixel densities are shown in FIG. 20A-C. Furthermore, the insoluble material obtained as a pellet after centrifugation of the aggregated solutions was resuspended in 1 ml H$_2$O containing 5 µM TFT, and the fluorescence (excitation at 446 nm and emission at 490 nm) was measured at RT. FIG. 20D shows normalized data for TFT binding (filled symbols) to insoluble material (reflecting the formation of fibrils) and mAb20 binding (open symbols) to soluble material (reflecting the formation of oligomers).

---

The invention claimed is:

1. A binding protein comprising a binding region capable of binding to Aβ$_{42}$ prefibrillar oligomers with β-structure, said antigen-binding region comprising:
   SEQ ID NO:1: GFSLSTFGSGVS or an amino acid sequence having at least 85% sequence identity to SEQ ID NO:1;
   SEQ ID NO:2: HIYWDDDKH or an amino acid sequence having at least 85% sequence identity to SEQ ID NO:2;
   SEQ ID NO:3: RESHYYGSGYYFDY or an amino acid sequence having at least 85% sequence identity to SEQ ID NO:3;
   SEQ ID NO:4: RASSSVSYMH or an amino acid sequence having at least 85% sequence identity to SEQ ID NO:4;
   SEQ ID NO:5: ATSNLAS or an amino acid sequence having at least 85% sequence identity to SEQ ID NO:5; and
   SEQ ID NO:6: QQWRSDPLT or an amino acid sequence having at least 85% sequence identity to SEQ ID NO:6;
   wherein said amino acid sequence having at least 85% sequence identity to SEQ ID NO:1, SEQ ID NO:2, SEQ ID NO:3, SEQ ID NO:4, SEQ ID NO:5 or SEQ ID NO:6 has one or more conservative amino acid substitutions compared to SEQ ID NO:1, SEQ ID NO:2, SEQ ID NO:3, SEQ ID NO:4, SEQ ID NO:5 or SEQ ID NO:6, said conservative amino acid substitutions are selected among the group consisting of Gly, Ala; Val, Ile, Leu; Asp, Glu; Asn, Gln; Ser, Thr; Lys, Arq; and Phe, Tyr.

2. The binding protein according to claim 1, wherein said binding protein is an antibody or an antibody fragment.

3. The binding protein according to claim 2, wherein said antibody is a monoclonal antibody.

4. The binding protein according to claim 2, wherein said antibody is a humanized antibody or a chimeric antibody.

5. The binding protein according to claim 2, wherein said antibody or antibody fragment is selected the group consisting of a single chain antibody, a Fv fragment, a scFv fragment, a Fab fragment, a F(ab')$_2$ fragment, a Fab' fragment, a Fd fragment, a dAb F, a scFv-Fc fragment, a nanobody, and a diabody.

6. A pharmaceutical composition comprising a binding protein according to claim 1 and a pharmaceutically acceptable carrier or excipient.

7. A method for treatment of an amyloid disease, comprising administering a pharmaceutical effective amount of a binding protein according to claim 1 to a subject in need of such treatment.

8. The method according to claim 7, wherein said amyloid disease is Alzheimer's disease.

9. A method for identifying a chemical substance which affects aggregation process of fibrillogenic proteins and peptides, said method comprising:
   adding said chemical substance to a solution of a fibrillogenic protein or peptide;
   determining if said chemical substance affects aggregation of said fibrillogenic protein or peptide, or if said chemical substance affects stability of pre-formed aggregates of said fibrillogenic protein or peptide, by assaying for existence of aggregates reactive against a binding protein according to claim 1; and
   identifying said chemical substance as potentially suitable for treatment of a disease caused by or related to formation of aggregates of said fibrillogenic protein or peptide.

* * * * *

SEQUENCE LISTING

```
<160> NUMBER OF SEQ ID NOS: 10

<210> SEQ ID NO 1
<211> LENGTH: 12
<212> TYPE: PRT
<213> ORGANISM: Mus musculus

<400> SEQUENCE: 1

Gly Phe Ser Leu Ser Thr Phe Gly Ser Gly Val Ser
1               5                   10

<210> SEQ ID NO 2
<211> LENGTH: 9
<212> TYPE: PRT
<213> ORGANISM: Mus musculus

<400> SEQUENCE: 2

His Ile Tyr Trp Asp Asp Asp Lys His
1               5

<210> SEQ ID NO 3
<211> LENGTH: 14
<212> TYPE: PRT
<213> ORGANISM: Mus musculus

<400> SEQUENCE: 3

Arg Glu Ser His Tyr Tyr Gly Ser Gly Tyr Tyr Phe Asp Tyr
1               5                   10
```

```
<210> SEQ ID NO 4
<211> LENGTH: 10
<212> TYPE: PRT
<213> ORGANISM: Mus musculus

<400> SEQUENCE: 4

Arg Ala Ser Ser Ser Val Ser Tyr Met His
1               5                   10

<210> SEQ ID NO 5
<211> LENGTH: 7
<212> TYPE: PRT
<213> ORGANISM: Mus musculus

<400> SEQUENCE: 5

Ala Thr Ser Asn Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Trp Arg Ser Asp Pro Leu Thr
1               5

<210> SEQ ID NO 7
<211> LENGTH: 372
<212> TYPE: DNA
<213> ORGANISM: Mus musculus
<220> FEATURE:
<221> NAME/KEY: CDS
<222> LOCATION: (1)..(372)

<400> SEQUENCE: 7 cag gtt act ctg aaa gag tct ggc cct ggt ata tcg cag ccc tcc cag        48
Gln Val Thr Leu Lys Glu Ser Gly Pro Gly Ile Ser Gln Pro Ser Gln
1               5                   10                  15 acc ctc agt ctg acc tgt tct ttc tct ggg ttt tca ctg agc act ttt        96
Thr Leu Ser Leu Thr Cys Ser Phe Ser Gly Phe Ser Leu Ser Thr Phe
            20                  25                  30 ggt tcg ggt gtg agc tgg att cgt cag cct tca ggg aag ggt ctg gag       144
Gly Ser Gly Val Ser Trp Ile Arg Gln Pro Ser Gly Lys Gly Leu Glu
        35                  40                  45 tgg ctg gca cac att tat tgg gat gat gac aag cac tat aac cca tcc       192
Trp Leu Ala His Ile Tyr Trp Asp Asp Asp Lys His Tyr Asn Pro Ser
    50                  55                  60 ttg aag agc cgg ctc aca atc tcc aag gat acc tcc aac aac cag gtt       240
Leu Lys Ser Arg Leu Thr Ile Ser Lys Asp Thr Ser Asn Asn Gln Val
65                  70                  75                  80 ttc ctc aag atc acc act gtg gac act gca gat act gcc aca tac ttc       288
Phe Leu Lys Ile Thr Thr Val Asp Thr Ala Asp Thr Ala Thr Tyr Phe
                85                  90                  95 tgt gct cga aga gag tct cat tac tac ggt agt ggc tac tac ttt gac       336
Cys Ala Arg Arg Glu Ser His Tyr Tyr Gly Ser Gly Tyr Tyr Phe Asp
            100                 105                 110 tac tgg ggc caa ggc acc act ctc aca gtc tcc tca                       372
Tyr Trp Gly Gln Gly Thr Thr Leu Thr Val Ser Ser
        115                 120

<210> SEQ ID NO 8
<211> LENGTH: 124
<212> TYPE: PRT
```

-continued

<213> ORGANISM: Mus musculus

<400> SEQUENCE: 8

Gln Val Thr Leu Lys Glu Ser Gly Pro Gly Ile Ser Gln Pro Ser Gln
1               5                   10                  15

Thr Leu Ser Leu Thr Cys Ser Phe Ser Gly Phe Ser Leu Ser Thr Phe
            20                  25                  30

Gly Ser Gly Val Ser Trp Ile Arg Gln Pro Ser Gly Lys Gly Leu Glu
        35                  40                  45

Trp Leu Ala His Ile Tyr Trp Asp Asp Lys His Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Thr Val Asp Thr Ala Asp Thr Ala Thr Tyr Phe
                85                  90                  95

Cys Ala Arg Arg Glu Ser His Tyr Tyr Gly Ser Gly Tyr Tyr Phe Asp
            100                 105                 110

Tyr Trp Gly Gln Gly Thr Thr Leu Thr Val Ser Ser
        115                 120

<210> SEQ ID NO 9
<211> LENGTH: 318
<212> TYPE: DNA
<213> ORGANISM: Mus musculus
<220> FEATURE:
<221> NAME/KEY: CDS
<222> LOCATION: (1)..(318)

<400> SEQUENCE: 9 caa att gtt ctc acc cag tct cca gca atc ctg tct tca tct cca ggg      48
Gln Ile Val Leu Thr Gln Ser Pro Ala Ile Leu Ser Ser Ser Pro Gly
1               5                   10                  15 gag aag gtc aca atg act tgc agg gcc agt tca agt gta agt tac atg      96
Glu Lys Val Thr Met Thr Cys Arg Ala Ser Ser Ser Val Ser Tyr Met
            20                  25                  30 cac tgg tac cag cag aag cca gga tcc tcc ccc aaa ccc tgg att tat     144
His Trp Tyr Gln Gln Lys Pro Gly Ser Ser Pro Lys Pro Trp Ile Tyr
        35                  40                  45 gcc aca tcc aac ctg gct tct gga gtc cct gct cgc ttc agc ggc agt     192
Ala Thr Ser Asn Leu Ala Ser Gly Val Pro Ala Arg Phe Ser Gly Ser
    50                  55                  60 ggg tct ggg acc tct tac tct ctc aca atc agc aga gtg gag gct gaa     240
Gly Ser Gly Thr Ser Tyr Ser Leu Thr Ile Ser Arg Val Glu Ala Glu
65                  70                  75                  80 gat gct gcc act tat tac tgc cag cag tgg aga agt gac cca ctc acg     288
Asp Ala Ala Thr Tyr Tyr Cys Gln Gln Trp Arg Ser Asp Pro Leu Thr
                85                  90                  95 ttc ggt gct ggg acc aag ctg gag ctg aaa                              318
Phe Gly Ala Gly Thr Lys Leu Glu Leu Lys
            100                 105

<210> SEQ ID NO 10
<211> LENGTH: 106
<212> TYPE: PRT
<213> ORGANISM: Mus musculus

<400> SEQUENCE: 10

Gln Ile Val Leu Thr Gln Ser Pro Ala Ile Leu Ser Ser Ser Pro Gly
1               5                   10                  15

Glu Lys Val Thr Met Thr Cys Arg Ala Ser Ser Ser Val Ser Tyr Met

-continued

```
                20                  25                  30
His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
 65              70                  75                  80

Asp Ala Ala Thr Tyr Tyr Cys Gln Gln Trp Arg Ser Asp Pro Leu Thr
            85                  90                  95

Phe Gly Ala Gly Thr Lys Leu Glu Leu Lys
            100             105
```